United States Patent
Abe et al.

(10) Patent No.: US 9,254,115 B2
(45) Date of Patent: Feb. 9, 2016

(54) ULTRASONIC DIAGNOSTIC APPARATUS FOR CARDIAC WALL MOVEMENT MEASUREMENTS BY RE-TRACKING THE CARDIAC WALL

(75) Inventors: Yasuhiko Abe, Otawara (JP); Tetsuya Kawagishi, Nasushiobara (JP)

(73) Assignees: KABUSHIKI KAISHA TOSHIBA, Tokyo (JP); Toshiba Medical Systems Corporation, Otawara-shi (JP)

(*) Notice: Subject to any disclaimer, the term of this patent is extended or adjusted under 35 U.S.C. 154(b) by 763 days.

(21) Appl. No.: 12/695,397

(22) Filed: Jan. 28, 2010

(65) Prior Publication Data

US 2010/0198072 A1 Aug. 5, 2010

(30) Foreign Application Priority Data

Jan. 30, 2009 (JP) ................................. 2009-020678
Dec. 2, 2009 (JP) ................................. 2009-274675

(51) Int. Cl.
*A61B 8/08* (2006.01)

(52) U.S. Cl.
CPC ............... *A61B 8/08* (2013.01); *A61B 8/0883* (2013.01)

(58) Field of Classification Search
CPC ......... A61B 8/00; A61B 8/08; G01S 7/52042
USPC ........... 378/98.7; 382/131; 600/407, 410, 443
See application file for complete search history.

(56) References Cited

U.S. PATENT DOCUMENTS 6,175,614 B1* 1/2001 Jensen et al. ................. 378/98.7
6,453,187 B1* 9/2002 Prince et al. .................. 600/410

(Continued)

FOREIGN PATENT DOCUMENTS

| JP | 2007-117252 | 5/2007 |
| JP | 2007-143606 | 6/2007 |
| JP | 2009-448 | 1/2009 |

OTHER PUBLICATIONS

Goffinet et al., Assessment of subendocardial vs. subepicardial left ventricular rotation and twist using twodimensional speckle tracking echocardiography: comparison with tagged cardiac magnetic resonance, European Heart Journal (2009) 30, 608-617.*

(Continued)

*Primary Examiner* — Amanda Lauritzen Moher
*Assistant Examiner* — Serkan Akar
(74) *Attorney, Agent, or Firm* — Oblon, McClelland, Maier & Neustadt, L.L.P.

(57) ABSTRACT

In the case where a tracking process of a moving tissue performing a contraction movement and an expansion movement and represented by a cardiac wall is performed for one heartbeat from the ED1 to the ED2, a contour position (tracking point) initially set at the ES (End-Systole) is tracked until ED1 in accordance with movement information, the tracking point is rearranged and a position of a middle layer is set at the ED (End-Diastole), the rearranged tracking point including the position of the middle layer is tracked in accordance with the movement information already obtained, and then the tracking point is further tracked in the normal direction until the ED2. Alternatively, an initial reverse tracking process is performed from the ES to the ED1 by using plural middle layer path candidates, and a path passing through the tracking point existing on the middle layer or contours of inner and outer layers and rearranged at the ED1 is searched, thereby accurately creating and evaluating movement information of each of an endocardium and an epicardium of a cardiac wall.

26 Claims, 14 Drawing Sheets

(56) References Cited

U.S. PATENT DOCUMENTS

| | | | |
|---|---|---|---|
| 6,892,089 B1 * | 5/2005 | Prince et al. | 600/410 |
| 8,073,523 B2 * | 12/2011 | Moghaddam et al. | 600/410 |
| 8,094,899 B2 * | 1/2012 | Chouno | 382/128 |
| 2003/0171668 A1 * | 9/2003 | Tsujino et al. | 600/407 |
| 2005/0096543 A1 * | 5/2005 | Jackson et al. | 600/441 |
| 2005/0101863 A1 * | 5/2005 | Kawagishi et al. | 600/443 |
| 2006/0008138 A1 * | 1/2006 | Zhou et al. | 382/159 |
| 2008/0009734 A1 * | 1/2008 | Houle et al. | 600/443 |
| 2008/0077032 A1 * | 3/2008 | Holmes et al. | 600/523 |
| 2008/0267482 A1 * | 10/2008 | Abe et al. | 382/131 |
| 2008/0317316 A1 * | 12/2008 | Ohuchi et al. | 382/131 |
| 2009/0069680 A1 | 3/2009 | Abe | |
| 2010/0198072 A1 * | 8/2010 | Abe et al. | 600/443 |
| 2010/0278405 A1 * | 11/2010 | Kakadiaris et al. | 382/131 |

OTHER PUBLICATIONS

Yang et al, 3D Ultrasound Tracking of the Left Ventricle Using One-Step Forward Prediction and Data Fusion of Collaborative Trackers, CVPR 2008.*

Japanese Office Action issued Sep. 3, 2013, in Japan Patent Application No. 2009-274675 (with English translation).

* cited by examiner

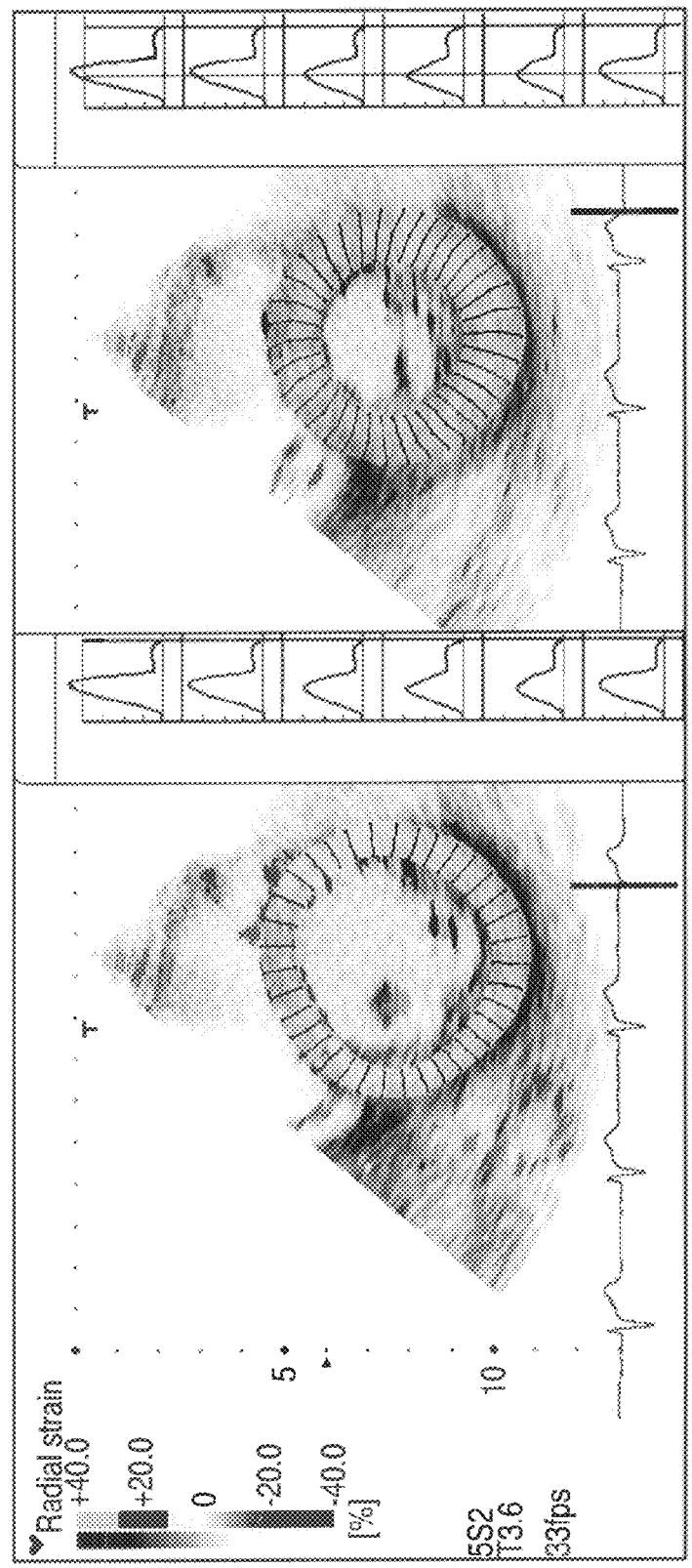
FIG. 4A Rearrange inner, outer, and middle layers at ED
FIG. 4B Inner and outer membranes (and middle layer) at ES after retracking process from ED toward ES

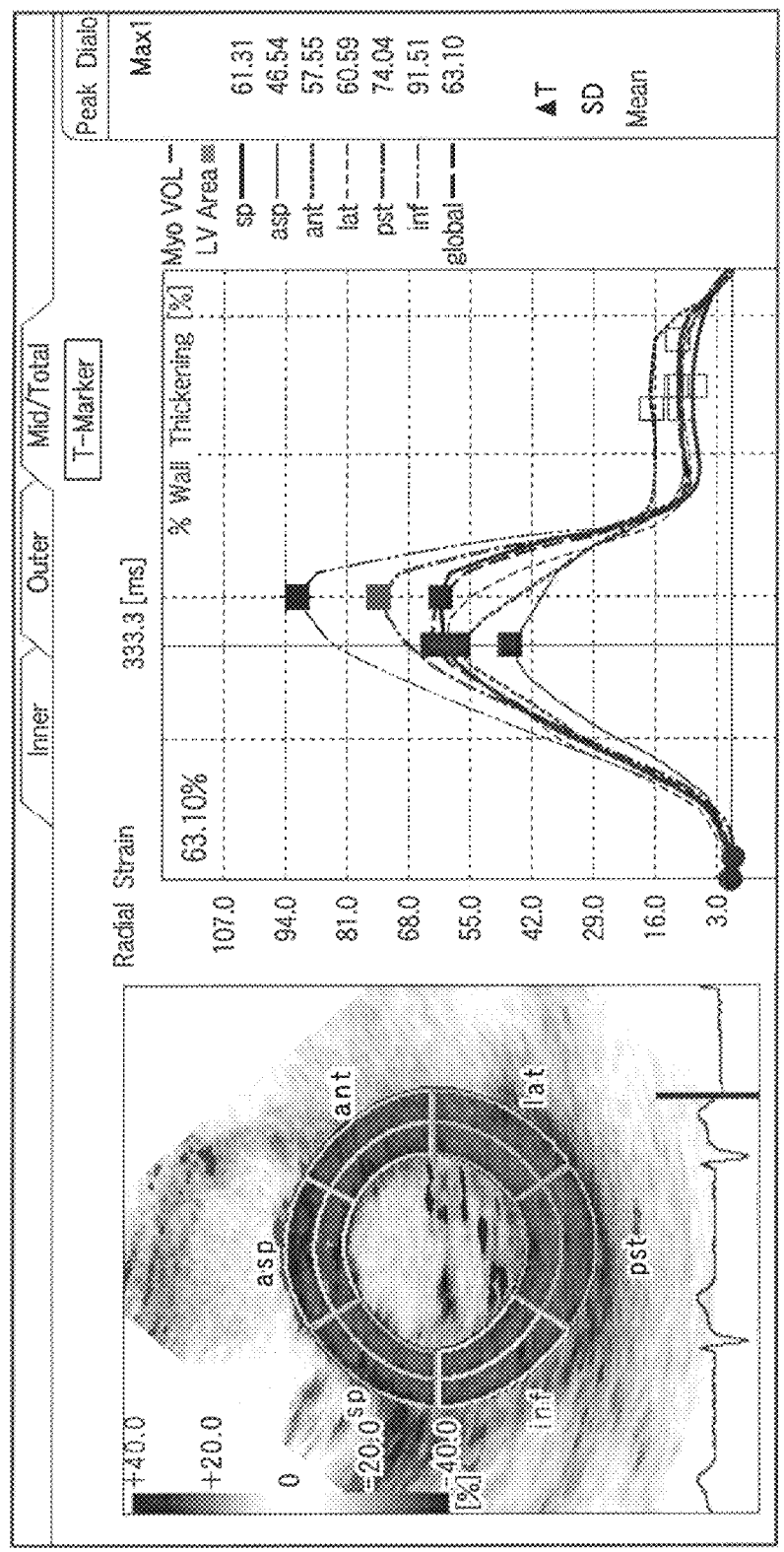
F I G. 6

ULTRASONIC DIAGNOSTIC APPARATUS FOR CARDIAC WALL MOVEMENT MEASUREMENTS BY RE-TRACKING THE CARDIAC WALL

CROSS-REFERENCE TO RELATED APPLICATIONS

This application is based upon and claims the benefit of priority from prior Japanese Patent Applications No. 2009-020678, filed Jan. 30, 2009; and No. 2009-274675, filed Dec. 2, 2009, the entire contents of both of which are incorporated herein by reference.

BACKGROUND OF THE INVENTION

1. Field of the Invention

The present invention relates to an ultrasonic diagnostic apparatus capable of obtaining tissue movement information such as cardiac wall movement information, an ultrasonic image processing apparatus performing an image process by using the tissue movement information obtained by the ultrasonic diagnostic apparatus, a medical image diagnostic apparatus, a medical image processing apparatus, an ultrasonic image processing method, and a medical image processing method.

2. Description of the Related Art

In the ultrasonic diagnosis, a heartbeat or a fetus's movement state may be obtained in real time just by touching a body surface with an ultrasonic probe and the ultrasonic diagnosis may be repeated due to the reliability thereof. In addition, since the size of the system of the ultrasonic diagnostic apparatus is smaller than other diagnostic apparatuses such as an X-ray diagnostic apparatus, a CT diagnostic apparatus, and an MRI diagnostic apparatus, the ultrasonic diagnosis may be easily performed by disposing the ultrasonic diagnostic apparatus at a position on the side of the bed. For this reason, the ultrasonic diagnosis is a simple diagnosis method. The size of the ultrasonic diagnostic apparatus used in the ultrasonic diagnosis is different depending on the types of the functions thereof, and a small-sized ultrasonic diagnostic apparatus which may be carried in one hand is developed. Unlike the X-ray diagnosis, the ultrasonic diagnosis has no influence regarding radiation exposure, and hence the ultrasonic diagnosis may be used for obstetrics or the home medical treatment.

In the diagnosis of the body tissue, it is very important to objectively and quantitatively evaluate the function of the body tissue such as a myocardium of a heart. Recently, various quantitative evaluation methods using the above-described ultrasonic diagnostic apparatus have been attempted by mainly exemplifying a heart. For example, as described in Japanese Unexamined Patent Application Publication No. 2003-175041 and Japanese Unexamined Patent Application Publication No. 2003-250804, a Speckle Tracking technique (hereinafter, referred to as "ST") is commercialized which detects a movement of a local region by performing a local pattern matching process on a two-dimensional or three-dimensional image, and calculates and displays local wall movement information such as displacement or strain. In addition, a method of displaying a "strain gauge" connecting a pair of two points for strain measurement using the ST method is known as described in, for example, Japanese Unexamined Patent Application Publication No. 2009-78136 and Japanese Patent Application No. 2008-160744. In the strain gauge display of the related art, a local strain gauge display for each wall thickness of the inner and outer half is also described, and hence it is possible to observe a detailed wall movement state in the inside of a myocardium having a multi-layer structure, for example, each of an endocardium and an epicardium.

Here, as an example of a detailed clinical significance for evaluating each of the endocardium and the epicardium of the inside of the myocardium, as shown in Kuwada Y et al: Transmural Heterogeneity of the Left Ventricular Wall: Sub-endocardial Layer and Subepicardial Layer. Jpn J Cardiol 2000; 35; 205-218, it is known that the radial strain is not uniform in the inside of the wall, for example, the expansion and contraction amount of an endocardium is two times larger than that of an epicardium in a healthy myocardium. Meanwhile, in most cardiac diseases represented by an ischemic cardiac disease, since disease occurs from the endocardium, when the strain of the endocardium is evaluated, it is possible to perform a more sensitive diagnosis. Particularly, in the case of a subendocardial ischemia, a case is described in which the radial strain of the epicardium compensatively increases in accordance with a decrease in the radial strain of the endocardium as shown in Kuwada Y et al, or Maruo T et al. Am J Physiol 2007; 292: H921-927, or T. Ishizu et al; "Impaired Subendocardial and Compensated Subepicardial Wall Thickening at Rest in Patients with Severe Coronary Stenosis but Visually Normal Wall Motion", JCS2008 abstract.

Incidentally, in the known method disclosed in Japanese Unexamined Patent Application Publication No. 2009-78136 and the like, a tracking method is shown which sets initial contours of an endocardium and an epicardium at the time phase ES (End-Systole) and determines a position of a middle layer as a middle point between the endocardium and the epicardium on the initial contours. When a tracking process is started by setting an initial contour at the time phase ED (End-Diastole) at the short axis image of the heart, the tracking process of the contour of the endocardium fails due to a reason (A) that a low-correlation echo pattern of the endocardium occurs in a boundary portion of the endocardium due to the out-of-plane motion influence.

That is, in order to highly precisely obtain the movement information of the tissue, the estimation of the movement vector is performed only in the tissue region. The tissue region is initially set by the initial contour, and is set by the contour tracked by using the movement information based on the estimated movement vector at the other time phases. Here, in consideration of the case where the movement vector has an incorrect direction due to a variation or noise of speckle, in the ST, generally a process is performed which spatially estimates plural movement vectors and removes the incorrect vectors through a statistical operation. In addition, when the movement information required for tracking the contour position as the target is obtained, it is desirable to perform a spatial interpolation by using the closest remained movement vectors which are selected after the statistical work.

In a series of ST processes, in the case where the low-correlation echo pattern occurs in the boundary portion of the endocardium due to the out-of-plane motion influence, the contour of the endocardium moves from a portion which has been the boundary of the myocardium tissue until now toward the inside of the cardiac chamber at the systole. At this time, when low-correlation pattern matching occurs, the accuracy of the movement information is influenced and deteriorated because the number of the highly precise remained movement vectors at the closest position becomes small, and hence the tracking process may easily fail.

On the contrary, in the case where the tracking process is started from the ES, when the reason (A) is reversed in time at the systole, the contour of the endocardium moves from a portion which has been the boundary of the myocardium tissue until now toward the inside of the myocardium. Then, since the number of the highly precise movement vectors obtained from the tissue portion is relatively large, the accuracy of the remained movement vectors is improved, and hence the tracking process rarely fails. As a result, compared with the case where the tracking process is started from the ED, it is possible to obtain higher accuracy in the case where the tracking process is started from the ES in the short axis image.

In such an analysis, in the known method, a problem arises in that the radial strain RS (t) for each of the endocardium and the epicardium cannot be accurately evaluated due to the following circumstances.

That is, the radial strain RS (t) is obtained as a radial strain of the length L (t) at each time phase (t) by the following expression by using a length between the endocardium and the epicardium in the wall thickness direction at the time phase ED which is set to a reference length L0.

$$RS(t)=100*(L(t)-L0)/L0[\%]$$ (Expression 1)

The RS (t) around the time phase ES has a peak value and the peak value of the RS reflects a local contraction ability of the myocardium.

Meanwhile, in order to evaluate the RS (t) for each of the endocardium and the epicardium, at the time phase ED, a position of a middle layer is set to a position where the wall thickness is equally divided into two segments, and a radial strain RS_inner (t) between the endocardium and the middle layer and a radial strain RS_outer (t) between the middle layer and the epicardium are obtained. At this time, in order to correctly evaluate the value of the RS (t) of each of the endocardium and the epicardium around the time phase ES, it is necessary to obtain the position of the middle layer by performing a tracking process from the ED toward the ES. If the tracking process of the positions of the endocardium and the epicardium is accurate, even when the tracking process is started from the ED, no particular problem arises. However, as described above, since the tracking accuracy of the position of endocardium is poor when the tracking process is started from the ED in the short axis image, it is not possible to accurately evaluate the RS of the entire wall thickness in addition to the evaluation for each of the endocardium and the epicardium.

When the tracking process is started from the ES in order to accurately evaluate the RS (t) of the entire wall thickness, the tracking process is performed from the ES toward the ED in the state where the position of the middle layer is set at the time phase ES as the position in which the wall thickness between the endocardium and the epicardium is equally divided into two segments. For this reason, the position of the middle layer at the ED after the tracking process is different from the originally determined position which is set at the ED as the position in which the wall thickness between the endocardium and the epicardium is equally divided into two segments.

The state of this problem is shown as a simple model in FIGS. 14A and 14B. For the simplification of the model, a one-dimensional model is supposed, the vertical axis corresponds to the wall thickness direction, and the horizontal axis corresponds to the time direction. As shown in the drawings, the values are set such that the RS_inner (ES)=160%, the RS_outer (ES)=80%, the wall thickness WT (ED)=10 mm. Accordingly, the wall thickness WT (ES)=22 mm. The endocardium equally divided into two segments at the ED is set to be expanded to two times larger than the epicardium.

As shown in FIG. 14A, when the middle layer is equally divided into two segments at the ED, the L0 of each of the endocardium and the epicardium is 5 mm. In addition, the position of the middle layer obtaining the RS (ES) equal to the value set at the ES is a position away from the epicardium by 9 mm and away from the endocardium by 13 mm.

Meanwhile, as shown in FIG. 14B, when the middle layer is equally divided into two segments at the ES, the position of the middle layer at the ES is a position away from the endocardium and the epicardium by 11 mm. Since the position is included in a region of the RS_inner (ES) set to 160%, when the backcalculation of the position of the middle layer at the ED is performed so that the RS_inner (ES)=160%, the position is obtained as a position away from the epicardium by 5.77 mm and away from the endocardium by 4.23 mm. In this case, due to the overvaluation of the epicardium compared with the value set such that RS_outer (ES)=91%, it is observed that the endocardium is more expanded than the epicardium by only 1.77 times.

BRIEF SUMMARY OF THE INVENTION

The present invention is contrived in consideration of the above-described circumstances, and an object of the invention is to provide an ultrasonic diagnostic apparatus, an ultrasonic image processing apparatus, a medical image diagnostic apparatus, a medical image processing apparatus, an ultrasonic image processing method, and a medical image processing method capable of more accurately evaluating radial strain of each of an endocardium and an epicardium of a heart.

According to an aspect of the present invention, there is provided an ultrasonic diagnostic apparatus including: a data obtaining unit which obtains two-dimensional or three-dimensional spatial receiving signals, obtained by scanning a periodically moving patient diagnosis portion through an ultrasonic wave, for a predetermined period equal to or more than one period; a data creating unit which creates two-dimensional or three-dimensional time-series ultrasonic image data by using the spatial receiving signals; a region-of-interest (ROI) setting unit which sets ROIs corresponding to inner and outer half of a tissue of the diagnosis portion on the ultrasonic image data at a first time phase during the predetermined period; a first tracking unit which performs a first tracking process of tracking position information of the ROIs at a time phase other than the first time phase by using movement information obtained from a movement vector estimating process including a pattern matching process; a middle layer setting unit which sets positions of one or more middle layers, equally dividing the inside of the ROIs into plural segments, on the ultrasonic image data at a second time phase as a reference of a periodic movement before the first time phase; and a second tracking unit which performs a second tracking process of tracking position information of the middle layers at each time phase during the predetermined period other than the second time phase by using the movement information.

According to another aspect of the present invention, there is provided an ultrasonic image processing apparatus including: a storage unit which stores two-dimensional or three-dimensional spatial receiving signals, obtained by scanning a periodically moving patient diagnosis portion through an ultrasonic wave, for a predetermined period equal to or more than one period; an ROI setting unit which sets ROIs corresponding to inner and outer half of a tissue of the diagnosis portion on two-dimensional or three-dimensional time-series ultrasonic image data by using the spatial receiving signals; a first tracking unit which performs a first tracking process of tracking position information of the ROIs at a time phase other than the first time phase by using movement information obtained from a movement vector estimating process including a pattern matching process; a middle layer setting unit which sets positions of one or more middle layers, equally dividing the inside of the ROIs into plural segments, on the ultrasonic image data at a second time phase as a reference of a periodic movement before the first time phase; and a second tracking unit which performs a second tracking process of tracking position information of the middle layers at each time phase during the predetermined period other than the second time phase by using the movement information.

According to yet another aspect of the present invention, there is provided a medical image diagnostic apparatus including: a data obtaining unit which obtains two-dimensional or three-dimensional time-series image data of a periodically moving patient diagnosis portion for a predetermined period equal to or more than one period; an ROI setting unit which sets ROIs corresponding to inner and outer half of a tissue of the diagnosis portion on the image data at a first time phase during the predetermined period; a first tracking unit which performs a first tracking process of tracking position information of the ROIs at a time phase other than the first time phase by using movement information obtained from a movement vector estimating process including a pattern matching process; a middle layer setting unit which sets positions of one or more middle layers, equally dividing the inside of the ROIs into plural segments, on the image data at a second time phase as a reference of a periodic movement before the first time phase; and a second tracking unit which performs a second tracking process of tracking position information of the middle layers at each time phase during the predetermined period other than the second time phase by using the movement information.

According to yet another aspect of the present invention, there is provided a medical image processing apparatus including: a storage unit which stores two-dimensional or three-dimensional time-series image data of a periodically moving patient diagnosis portion for a predetermined period equal to or more than one period; an ROI setting unit which sets ROIs corresponding to inner and outer half of a tissue of the diagnosis portion on the image data at a first time phase during the predetermined period; a first tracking unit which performs a first tracking process of tracking position information of the ROIs at a time phase other than the first time phase by using movement information obtained from a movement vector estimating process including a pattern matching process; a middle layer setting unit which sets positions of one or more middle layers, equally dividing the inside of the ROIs into plural segments, on the image data at a second time phase as a reference of a periodic movement before the first time phase; and a second tracking unit which performs a second tracking process of tracking position information of the middle layers at each time phase during the predetermined period other than the second time phase by using the movement information.

According to yet another aspect of the present invention, there is provided an ultrasonic image processing method which is performed on two-dimensional or three-dimensional spatial receiving signals, obtained by scanning a periodically moving patient diagnosis portion through an ultrasonic wave, for a predetermined period equal to or more than one period by using a medical workstation, the ultrasonic image processing method including: setting an ROI corresponding to inner and outer half of a tissue of the diagnosis portion on two-dimensional or three-dimensional time-series ultrasonic image data by using the spatial receiving signals; performing a first tracking process of tracking position information of the ROIs at a time phase other than the first time phase by using movement information obtained from a movement vector estimating process including a pattern matching process; setting positions of one or more middle layers, equally dividing the inside of the ROIs into plural segments, on the ultrasonic image data at a second time phase as a reference of a periodic movement before the first time phase; and performing a second tracking process of tracking position information of the middle layers at each time phase during the predetermined period other than the second time phase by using the movement information.

According to yet another aspect of the present invention, there is provided a medical image processing method which is performed on two-dimensional or three-dimensional time-series image data obtained from a periodically moving patient diagnosis portion for a predetermined period equal to or more than one period by using a medical workstation, the medical image processing method including: setting ROIs corresponding to inner and outer half of a tissue of the diagnosis portion on the image data at a first time phase during the predetermined period; performing a first tracking process of tracking position information of the ROIs at a time phase other than the first time phase by using movement information obtained from a movement vector estimating process including a pattern matching process; setting positions of one or more middle layers, equally dividing the inside of the ROIs into plural segments, on the image data at a second time phase as a reference of a periodic movement before the first time phase; and performing a second tracking process of tracking position information of the middle layers at each time phase during the predetermined period other than the second time phase by using the movement information.

BRIEF DESCRIPTION OF THE SEVERAL VIEWS OF THE DRAWING

FIGS. 4A and 4B are diagrams illustrating a process of rearranging a tracking point on inner and outer contours at a time phase ED1.

FIG. 6 is a diagram illustrating the effect obtained by the ultrasonic diagnostic apparatus according to the first embodiment.

DETAILED DESCRIPTION OF THE INVENTION

Figure 1:
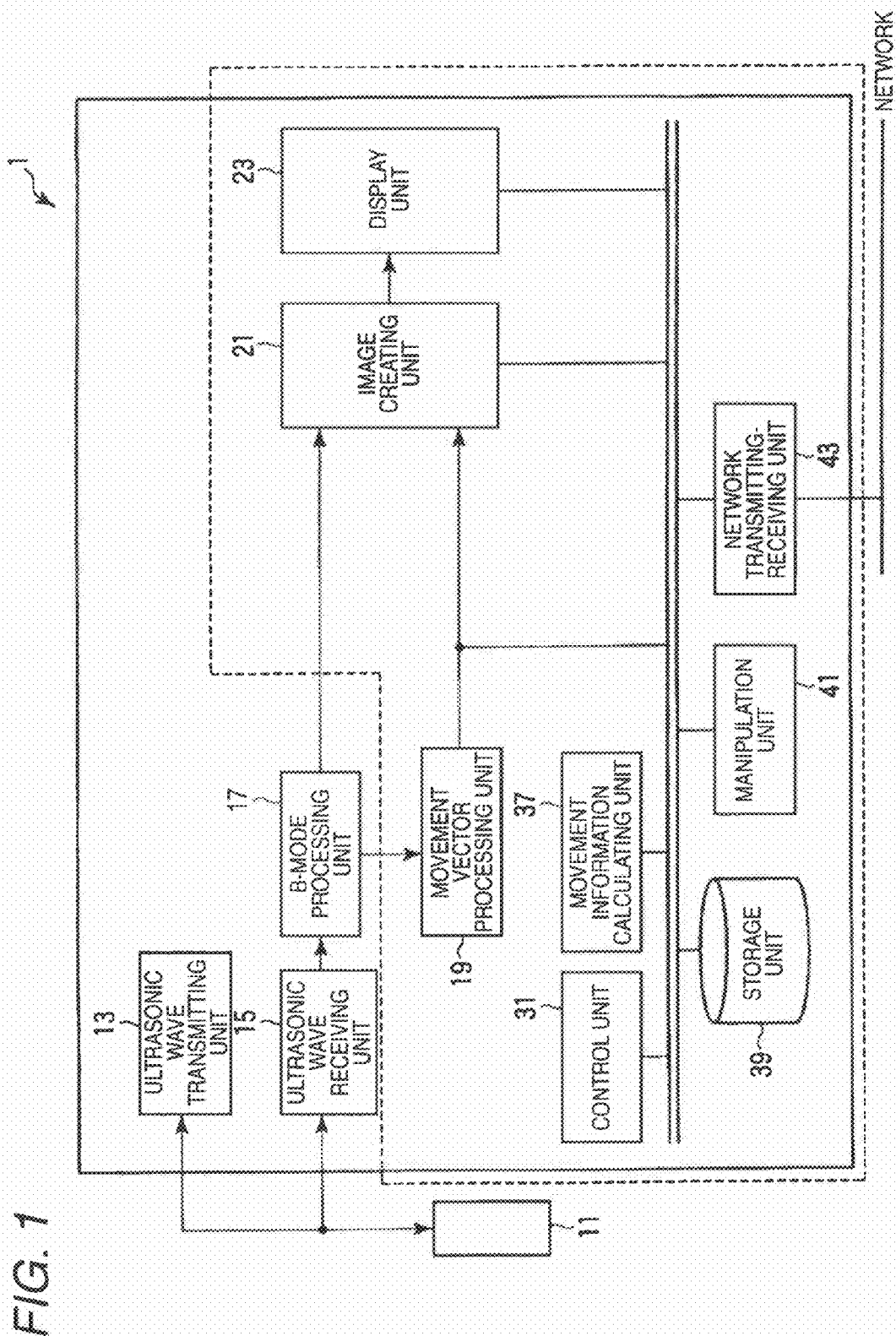
FIG. 1 is a configuration diagram of an ultrasonic diagnostic apparatus according to a first embodiment.

Hereinafter, first to third embodiments of the invention will be described with reference to the accompanying drawings. Additionally, in the following description, the same reference numerals will be given to the constituents substantially having the same function and configuration, and repetitive description thereof will only be made if necessary.

First Embodiment

Hereinafter, a first embodiment of the invention will be described with reference to the drawings. In the following description, the same reference numerals will be given to the constituents substantially having the same function and configuration, and repetitive description thereof will be only made if necessary.

In addition, in the first embodiment, a case will be described in which the technical spirit of the invention is applied to an ultrasonic diagnostic apparatus. However, the invention is not limited thereto, and the technical spirit of the invention may be applied to an ultrasonic image processing apparatus using a workstation, a personal computer, and the like.

Further, the functions realized by the constituents according to the first embodiment, and particularly, the functions realized by a movement vector processing unit 19, an image creating unit 21, and a movement information calculating unit 37 may be also realized in such a manner that a software program for executing the same processes as the constituents is installed in a computer such as a workstation or in the ultrasonic diagnostic apparatus and the like having a function as a computer, and is loaded on a memory. At this time, a program capable of causing the computer to execute the method may be distributed while being stored in a storage medium such as a magnetic disk (a floppy (trademark) disk, a hard disk, and the like), an optical disk (a CD-ROM, a DVD, and the like), or a semiconductor memory.

FIG. 1 is a configuration diagram of an ultrasonic diagnostic apparatus 1 according to the first embodiment. The ultrasonic diagnostic apparatus 1 includes an ultrasonic probe 11, an ultrasonic wave transmitting unit 13, an ultrasonic wave receiving unit 15, a B-mode processing unit 17, a movement vector processing unit 19, an image creating unit 21, a display unit 23, a control unit 31 (implemented by a central processing unit (CPU)), a movement information calculating unit 37, a storage unit 39, a manipulation unit 41, and a network transmitting-receiving unit 43. In addition, in the case where the invention is applied to the ultrasonic image processing apparatus, for example, the ultrasonic image processing apparatus includes the constituents inside the dotted line in FIG. 1.

The ultrasonic probe 11 generates ultrasonic waves on the basis of a driving signal output from the ultrasonic wave transmitting unit 13, and includes plural piezoelectric vibrators which convert waves reflected from a patient into electric signals, a matching layer which is provided in the piezoelectric vibrators, a backing member which prevents the ultrasonic waves from being transmitted backward from the piezoelectric vibrators, and the like. When the ultrasonic waves are transmitted from the ultrasonic probe 11 to the patient, various harmonic components are generated with the transmission of the ultrasonic waves due to nonlinearity of body tissue. A fundamental wave and a harmonic component constituting the transmitted ultrasonic wave are scattered backward due to a minute scattering or a boundary of acoustic impedance of the body tissue, and are received as reflected waves (echo) by the ultrasonic probe 11.

The ultrasonic wave transmitting unit 13 includes a delay circuit, a pulser circuit, and the like which are not shown in the drawings. The pulser circuit repeatedly generates rate pulses at a predetermined rate frequency fr Hz (period; 1/fr second) so as to form the transmitted ultrasonic waves. The delay circuit converges the ultrasonic waves for each channel into a beam shape and gives a delay time required for determining the transmitting directivity to each rate pulse. The ultrasonic wave transmitting unit 13 applies a driving pulse to each vibrator so as to form an ultrasonic beam toward a predetermined scan line at a timing based on the rate pulse.

The ultrasonic wave receiving unit 15 includes an amplifier circuit, an A/D converter, an adder, and the like which are not shown in the drawings. The amplifier circuit amplifies the echo signals obtained via the probe 11 for each channel. The A/D converter gives a delay time required for determining the receiving directivity to the amplified echo signals, and the amplified echo signals are subjected to an adding process by the adder. By means of the adding process, ultrasonic echo signals corresponding to a predetermined scan line are created.

The B-mode processing unit 17 creates B-mode signals corresponding to the amplitude magnitude of the ultrasonic echo signals by applying an envelope detecting process on the ultrasonic echo signals received by the ultrasonic wave receiving unit 15.

The movement vector processing unit 19 detects the movement position of the tissue by using a pattern matching process between two pieces of two-dimensional image data at different time phases or two pieces of volume data at different time phases, and obtains a movement vector (or a velocity) of each tissue on the basis of the movement position. In detail, the movement vector of the tissue is obtained in such a manner that an ROI in one piece of two-dimensional image data having the highest similarity to an ROI of the other of the two-dimensional image data is obtained, and a distance between the ROIs is obtained. In addition, when the magnitude of the movement vector (that is, movement amount) is divided by a time difference (a time difference between volume data) between frames of the two-dimensional image data, the movement velocity of the tissue is obtained. When the process is performed at each position on the two-dimensional image data frame by frame (or at each position on the three-dimensional image data volume by volume), spatio-temporal distribution data (movement vector information) for the velocity or displacement (movement vector) of the tissue is obtained.

The image creating unit 21 creates a B-mode ultrasonic image showing a two-dimensional distribution according to a predetermined tomography of the B-mode signal. In addition, the image creating unit 21 creates a strain gauge image for visualizing the displacement of each of the inner, outer, and middle layers as a line segment, and an image (movement information image) where the movement information is superimposed with a corresponding position on the ultrasonic image by using the movement information calculated by the movement information calculating unit 37.

As described below, the display unit 23 displays the ultrasonic image, the movement information image, the strain gauge image, and the like in a predetermined form on the basis of a video signal from the image creating unit 21. In addition, the display unit 23 displays a color bar showing the magnitude of the color-coded physical amount, a marker, or assistant information showing the anatomical position on the image.

The control unit 31 (implemented by a CPU) functions as an information processing device (calculator), and statically or dynamically controls the operation of the ultrasonic diagnostic apparatus. Particularly, the control unit 31 performs the movement information creating function to be described later by loading an exclusive program stored in the storage unit 39 on a memory (not shown).

The movement information calculating unit 37 calculates predetermined movement information such as a strain or a strain rate by using a result of the tracking process in the process in accordance with the movement information creating function to be described later.

The storage unit 39 is a storage medium such as a magnetic disk (a floppy (trademark) disk, a hard disk, and the like), an optical disk (a CD-ROM, a DVD, and the like), or a semiconductor memory, and is able to read information stored thereon. The storage unit 39 stores a transmitting-receiving condition, a predetermined scan sequence, raw data or ultrasonic image data (for example, tissue image data photographed in a tissue Doppler mode, a B-mode, or the like) corresponding to each time phase, volume data created in advance for each time phase, spatio-temporal distribution data for the velocity or the movement vector of the tissue, a program for realizing the movement information creating function to be described later, diagnostic information (a patient ID, a doctor's opinion, and the like), a diagnostic protocol, a body mark creating program, and the like.

The manipulation unit 41 is connected to the apparatus body, and includes a mouse, a track ball, a mode selection switch, a keyboard, and the like which are used to allow an operator to input various instructions, ROI (region of interest) setting instructions, various image quality condition setting instructions, arbitrary tissue movement information selection, and the like to the ultrasonic diagnostic apparatus 1.

The network transmitting-receiving unit 43 is a unit which transmits information to and receives information from other devices through a network. The data such as an ultrasonic image or an analysis result obtained in the ultrasonic diagnostic apparatus 1 is able to be transmitted to other devices through a network by the network transmitting-receiving unit 43.

Movement Information Creating Function

Next, the movement information creating function of the ultrasonic diagnostic apparatus 1 will be described. In the case where the tracking process of a moving tissue performing a contraction movement and an expansion movement and represented by a cardiac wall is performed for one heartbeat from ED1 to ED2, the movement information creating function is used to accurately create and evaluate the movement information of each of the endocardium and the epicardium of the cardiac wall in such a manner that the reverse tracking process of the contour position (tracking point) initially set at the ES (End-Systole) is performed in time until the ED1 (End-Diastole), the rearrangement process is performed at the ED, the retracking process of the rearranged tracking point is performed in accordance with the movement information already obtained, and then the tracking process (the tracking process including the reverse tracking process, the rearrangement process, and the retracking process) is further performed in the normal direction until the ED2.

Figure 2:
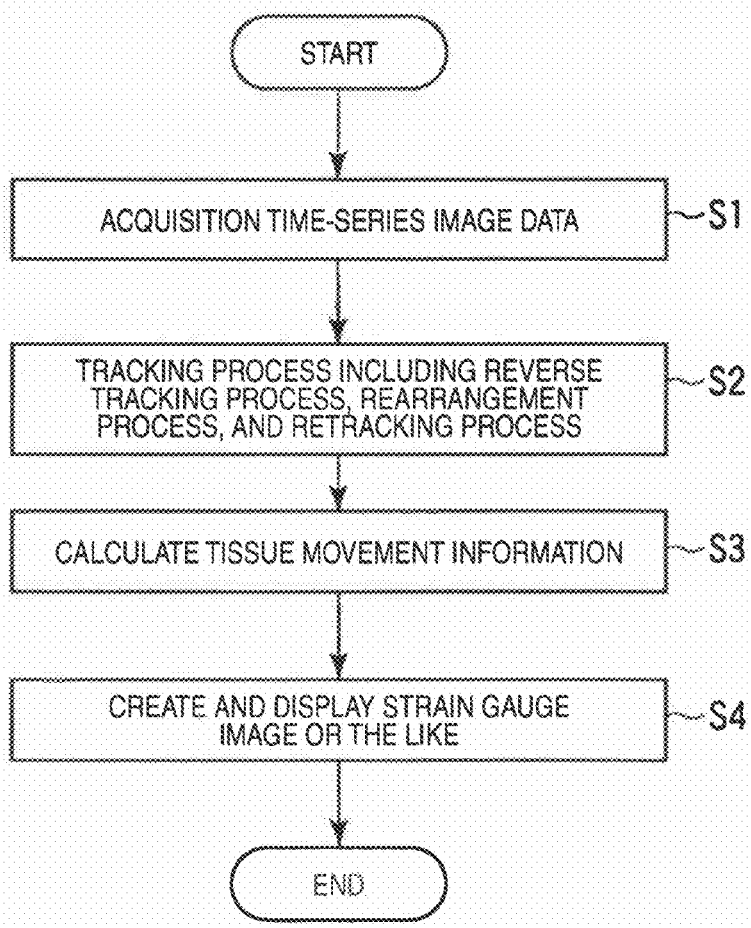
FIG. 2 is a flowchart showing a sequence of a process (movement information creating process) in accordance with a movement information creating function.
Figure 3:
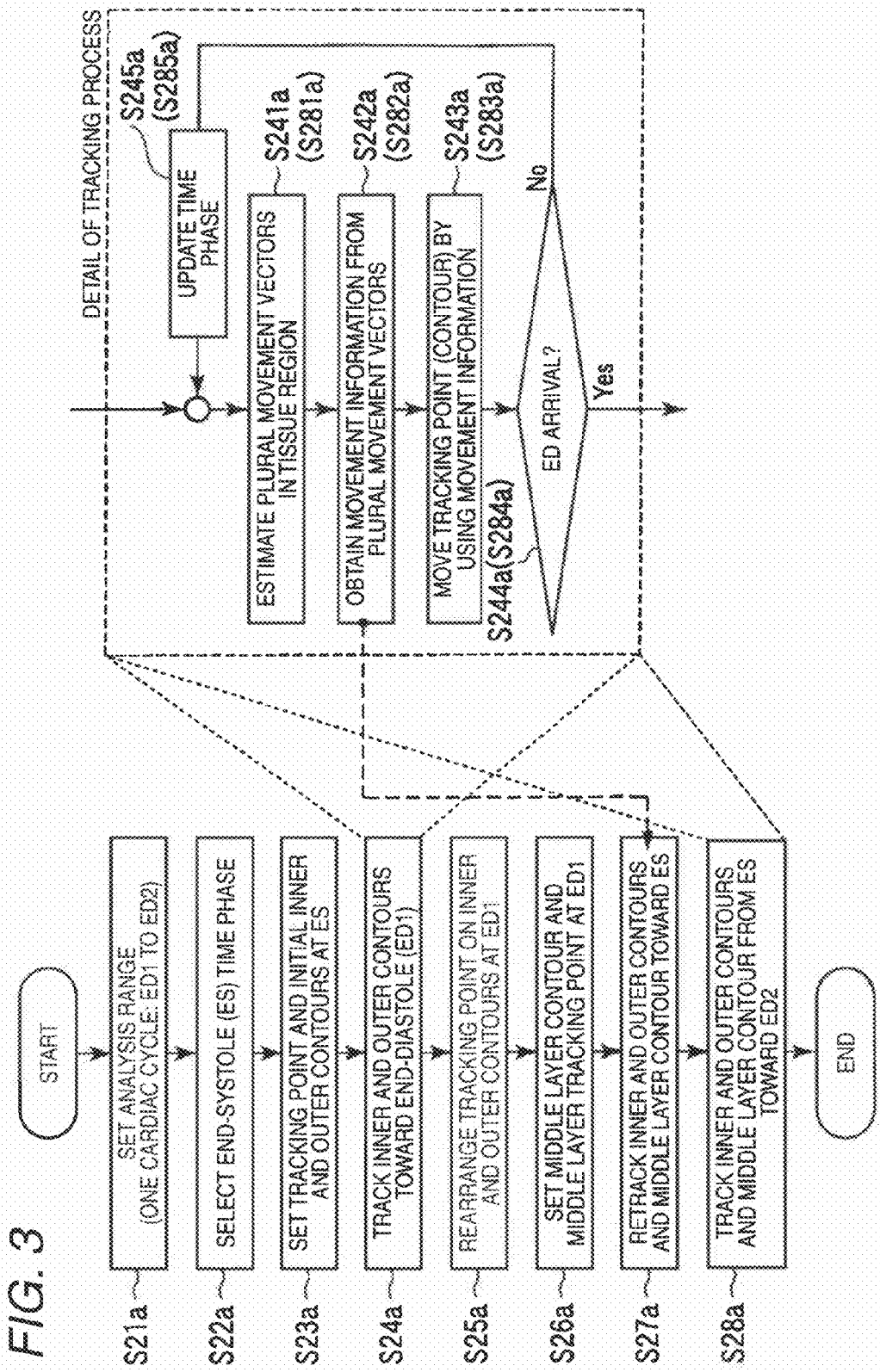
FIG. 3 is a flowchart showing a detailed sequence of a tracking process including a reverse tracking process, a rearrangement process, and a retracking process according to the first embodiment.

FIG. 2 is a flowchart showing a sequence of a process (movement information creating process) in accordance with the movement information creating function. FIG. 3 is a flowchart showing a detailed sequence of "the tracking process including the reverse tracking process, the rearrangement process, and the retracking process" of Step S2 in FIG. 2. Hereinafter, the contents of the movement information creating process will be described with reference to the respective drawings.

Acquisition of Time-Series Data: Step S1

First, two-dimensional image data (hereinafter, referred to as the "time-series two-dimensional image data group") of a time series throughout a period equal to or more than one heartbeat is acquired from an entire heart or a desired observation portion of a heart of a certain patient (Step S1). That is, two-dimensional image data of a time series (at least one heartbeat) based on a certain time is acquired from the desired observation portion of the heart of the certain patient through a cardiac apex approach.

Tracking Process including Reverse Tracking Process, Rearrangement Process, and Retracking Process: Step S2

Subsequently, as shown in FIG. 3, the tracking process including the reverse tracking process, the rearrangement process, and the retracking process is performed.

That is, in order to perform the process shown in FIG. 3, the control unit 31 shown in FIG. 1 sets a movement information analysis range of one heartbeat (ED1 to ED2) in the time-series two-dimensional image data, and selects the time phase ES (End-Systole time phase) in the one heartbeat (Step S21*a* and Step S22*a*). In addition, a method of setting the one heartbeat (ED1 to ED2) and selecting the time phase ES is not particularly limited. For example, any method such as a method based on the ECG signal and a manual method in accordance with the input from the manipulation unit 41 may be used.

Subsequently, the control unit 31 sets the initial contours (initial inner and outer contours) of the endocardium and the epicardium at the time phase ES and the tracking point as the target of the tracking process (Step S23*a*). That is, the control unit 31 displays the ultrasonic image on the display unit 23 by using the two-dimensional image data at the time phase ES. On the displayed ultrasonic image, a papillary muscle or a chorda tendinea is displayed in addition to the endocardium and the epicardium. The operator designates the contour of the endocardium through the manipulation unit 41 while observing the displayed ultrasonic image so that the papillary muscle or the chorda tendinea displayed on the image data of the heart is not included. In addition, in the epicardium, in the same manner, the contour of the epicardium is designated on the ultrasonic image at the time phase ES through the manipulation unit 41. When the initial contours of the endocardium and the epicardium at the time phase ES are set by the operator, the movement vector processing unit 19 sets each point (tracking point) forming the set initial contours of the endocardium and the epicardium.

Subsequently, the movement vector processing unit 19 performs the reverse tracking process of the inner and outer contours (that is, the tracking point) toward the time phase ED1 (End-Diastole time phase), and obtains the coordinate information of the configuration points of the inner and outer contours at each time phase (Step S24a). That is, the movement vector processing unit 19 estimates plural movement vectors of the tissue region by performing a pattern matching process using a speckle pattern between the two-dimensional image data at the time phase ES and the two-dimensional image data temporally adjacent thereto from the time phase ES toward the time phase ED1 (Step S241a), and obtains the movement information of each tracking point by averaging the estimated plural movement vectors (Step S242a). The movement vector processing unit 19 tracks the inner and outer contours at the subsequent time phase by moving the tracking point (and the inner and outer contours formed by the tracking point) in accordance with the obtained movement information (Step S243a). The tracking process is performed by sequentially updating the time phase until the time phase ED1 (End-Diastole time phase) (Step S244a and Step S245a).

Subsequently, the movement vector processing unit 19 rearranges the tracking points of the inner and outer contours at the time phase ED1 (Step S25a). That is, as shown in FIG. 4A, the movement vector processing unit 19 rearranges the tracking points arranged on the contours so that the endocardium and the epicardium are perpendicular to the contours at the time phase ED1. In FIG. 4A, an example is shown in which the positions of the tracking points on the contour of the epicardium are rearranged so as to be perpendicular to the endocardial surface, but the positions of the tracking points on the contour of the endocardium may be rearranged so as to be perpendicular to the epicardial surface. Alternatively, the positions of the tracking points on the contours of the endocardium and the epicardium may be rearranged. After the tracking points are rearranged, the movement vector processing unit 19 sets a middle layer tracking point at the time phase ED1 as a middle point position between the endocardium and the epicardium. Accordingly, it is possible to obtain a radial strain gauge display at the time phase ED1 even when the initial contours of the endocardium and the epicardium are set at the time phase ES.

Subsequently, the movement vector processing unit 19 retracks the positions of the middle layer and the endocardium or the epicardium on the rearranged contours from ED1 toward ES by using the movement information obtained in the process of the ST method in Step S24a. As a result of the retracking process, it is understood that the direction of the gauge between the endocardium and the epicardium is not perpendicular to the endocardial surface throughout the entire segments at the time phase ES as shown in FIG. 4B. Particularly, when the portion from the anterior wall to the septal wall and the portion from the posterior wall to the lateral wall are carefully observed, it is necessary to pay attention to the observation result that the bending direction of the U-shaped strain gauge is opposite to that of the related art.

Subsequently, the movement vector processing unit 19 obtains the coordinate information of the configuration points of the inner and outer contours at each of the other time phases by performing the tracking process from the time phase ES toward the time phase ES2 using the inner and outer contours and the middle layer contour obtained in Step S27a (Step S28a). The contents of the tracking process are substantially the same as those shown in Step S241a to Step S245a.

Calculation of Tissue Movement Information: Step S3

The movement information calculating unit 37 calculates, for example, a radial strain RS (t) at an arbitrary time t on the basis of the coordinate information of each point forming the inner and outer contours and the middle layer contour at each cardiac time phase.

Creating and Displaying of Strain Gauge Image: Step S4

The image creating unit 21 creates a strain gauge image including the strain gauge in which the corresponding contours of the endocardium, the middle layer, and the epicardium are connected by a line segment (strain gauge) for each time phase on the basis of the coordinate information of each point forming the inner and outer contours and the middle layer contour at each cardiac time phase. In addition, the image creating unit 21 creates a predetermined image in which assistant information (that is, character information of Sept/Ant/Lat/Post/Inf) for the orientation of the anatomical segment of the myocardium portion of each image and calculated tissue movement information is color-coded, if necessary. In addition, the anatomical segment is set on the image as the frame line formed by the position of the thickness-direction division line for dividing at least one of contour positions of the ROIs corresponding to the endocardium and the epicardium, an contour position corresponding to the middle layer, and the ROI into a predetermined number of segments. The control unit 31 controls the display unit 23 such that the created strain gauge image or the like is displayed in a predetermined form.

Effect

The effect obtained by the ultrasonic diagnostic apparatus will be described below by the comparison with the related art.

Figures 5A, 5B:
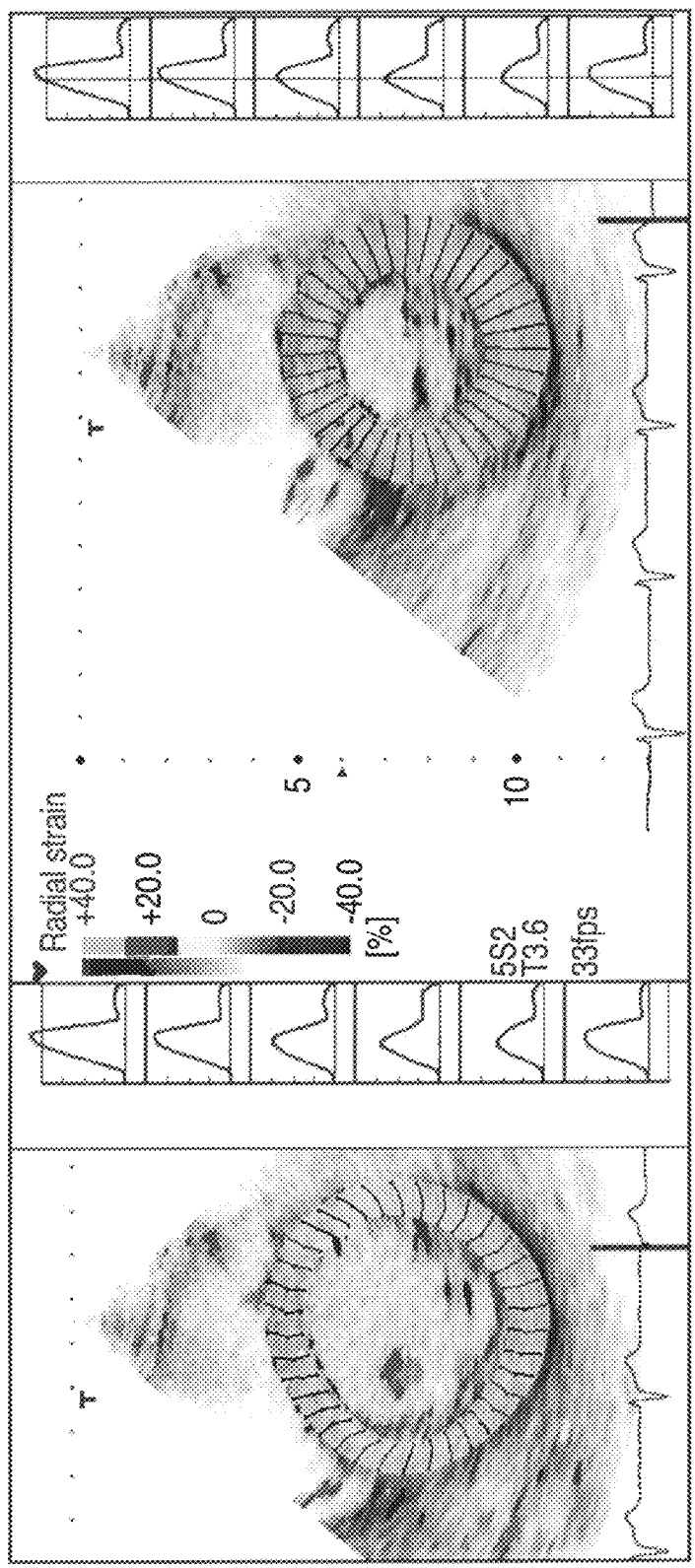
FIGS. 5A and 5B are diagrams illustrating an effect obtained by the ultrasonic diagnostic apparatus according to the first embodiment.

FIGS. 5A and 5B are an example of the strain gauge display of the related art. In FIG. 5A, the initial contours are set at the positions of the endocardium and the epicardium at the time phase ES (End-Systole), a certain position of an endocardium and a position where the radial line with respect to the endocardial surface intersects the epicardium are connected by a line segment (strain gauge), and the segments are displayed at plural positions. In addition, the position of the middle layer is given as the middle point between the endocardium and the epicardium at the phase ES (End-Systole). Meanwhile, FIG. 5B shows the ED (End-Diastole), and shows the result in which each position of the line segments is tracked by the ST method until the ED (End-Diastole). Here, in the related art, it is understood that the direction of the gauge between the endocardium and the epicardium throughout the entire segments at the time phase ED after the tracking process is not perpendicular to the endocardial surface. Particularly, when the portion from the anterior wall to the septal wall and the portion from the posterior wall to the lateral wall are carefully observed, it is observed that the strain gauge is bent in a U-shape. That is, in these portions, the rotation component of the position of the middle layer generated from the ES to the ED is relatively different from the rotation component of the positions of the endocardium and the epicardium. Likewise, even in the related art, the complex wall movement caused by the multi-layer structure of the myocardium can be intuitively recognized, as already known.

Meanwhile, in the strain gauge image obtained by the ultrasonic diagnostic apparatus exemplified in FIGS. 4A and 4B, a method of setting the position of the middle layer contour and a tracking method are different from those of the related art. That is, the tracking process is performed in such a manner that the tracking process of the contour position (tracking point) initially set at the ES (End-Systole) is performed in accordance with the movement information until the ED (End-Diastole), the rearrangement process (resetting process) is performed at the ED (End-Systole), and the retracking process of the rearranged tracking point is performed in accordance with the movement information already obtained.

Likewise, in the case where the strain gauge image of the related art is compared with the strain gauge image obtained by the ultrasonic diagnostic apparatus according to the invention, a first effect of the strain gauge image obtained by the ultrasonic diagnostic apparatus is that the time phase as the reference of the observation is changed from the ES to the ED. For example, in the case where a certain portion of the endocardium rotates in the clockwise direction by +20 degrees and the corresponding point of the epicardium of the strain gauge rotates by +10 degrees from the ED to the ES, in the related art, the rotation difference of 10 degrees between the endocardium and the epicardium is observed on the image at the ED. This means that the endocardium rotates by −20 degrees and the epicardium rotates by −10 degrees from the ES. Accordingly, the strain gauge starts to move from the deviated position at the ED, and is displayed as a straight line at the ES with the passing of time. On the contrary, in the ultrasonic diagnostic apparatus according to the invention, the rotation difference of 10 degrees between the endocardium and the epicardium is constant. However, the strain gauge disposed in a straight line starts to move at the ED, and the rotation component gradually grows in correspondence to the rotation difference between the endocardium and the epicardium generated with the passing of time. Accordingly, it is observed that the position of the endocardium rotates by +20 degrees and the position of the epicardium rotates by +10 degrees at the time phase ES. Likewise, in the ultrasonic diagnostic apparatus according to the invention, it is easy to intuitively understand the state where the endocardium and the epicardium individually rotate with the passing of time.

In addition, a second effect of the strain gauge image obtained by the ultrasonic diagnostic apparatus according to the invention is that the position of the middle layer is tracked by dividing the positions of the endocardium and the epicardium into two segments at the ED. Accordingly, since the problem of the related art is solved, it is possible to accurately evaluate the RS (t) in which the endocardium and the epicardium are separated. At this time, the new estimation of the movement information is not performed again in accordance with the ST method in the normal direction by setting the contours of the endocardium and the epicardium after the rearrangement process at the ED as the initial contours. This is because the tracking accuracy of the endocardium deteriorates due to the above-described reason when the estimation of the movement information is performed again. Accordingly, as the movement information used in the normal retracking process of the rearranged point from the ED to the ES, the information obtained by the initial reverse tracking process from the ES to the ED is kept and used again, thereby improving the tracking accuracy of the rearranged point. Of course, in the case where the movement information (movement vector) obtained by the initial reverse tracking process is V, −V is used for the normal retracking process in the reverse time direction. In addition, by using the position information of the contours of the endocardium and the epicardium obtained by the initial reverse tracking process, it is desirable to appropriately control the normal retracking process so as to pass through the contours of the endocardium and the epicardium.

In addition, regarding the position of the middle layer, on the assumption that there is a frame rate condition for allowing the speckle pattern variation with the strain to be sufficiently small, when the estimation positions of the movement vectors are provided at plural points inside the myocardium, it is possible to perform the normal retracking process with a high degree of accuracy by using the movement information estimated in the reverse direction.

Figure 7:
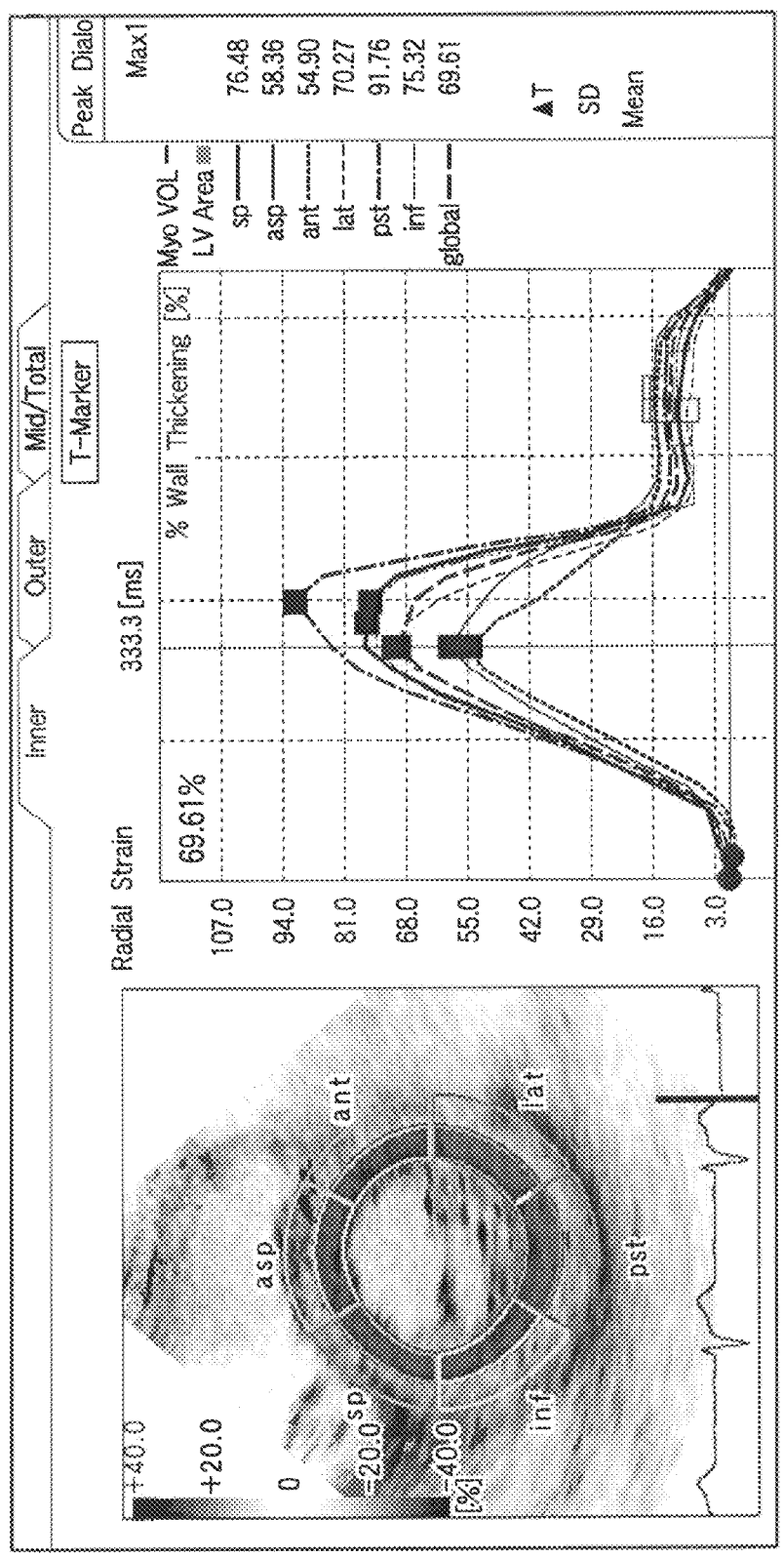
FIG. 7 is a diagram illustrating the effect obtained by the ultrasonic diagnostic apparatus according to the first embodiment.
Figure 8:
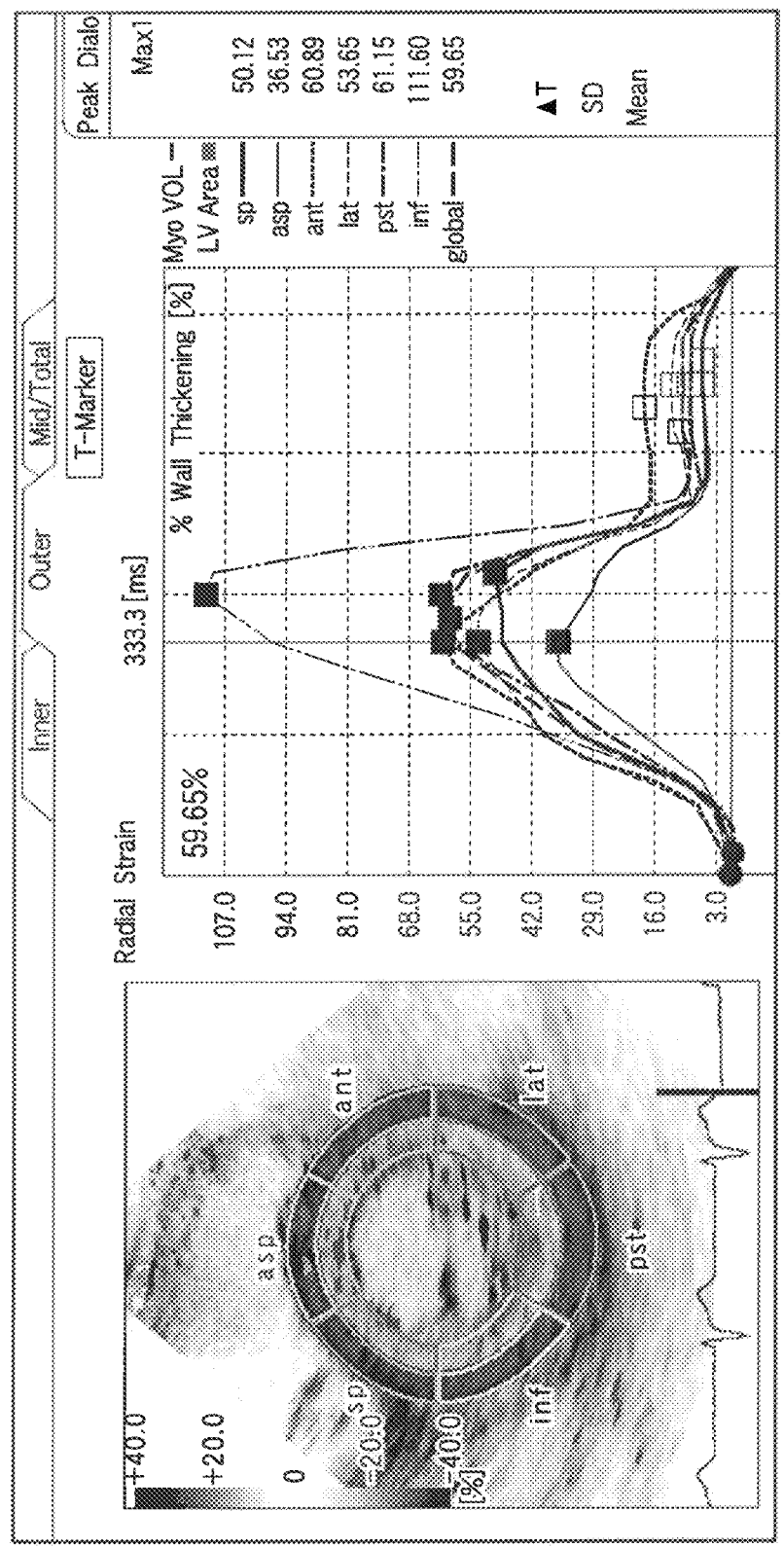
FIG. 8 is a diagram illustrating the effect obtained by the ultrasonic diagnostic apparatus according to the first embodiment.
Figure 9:
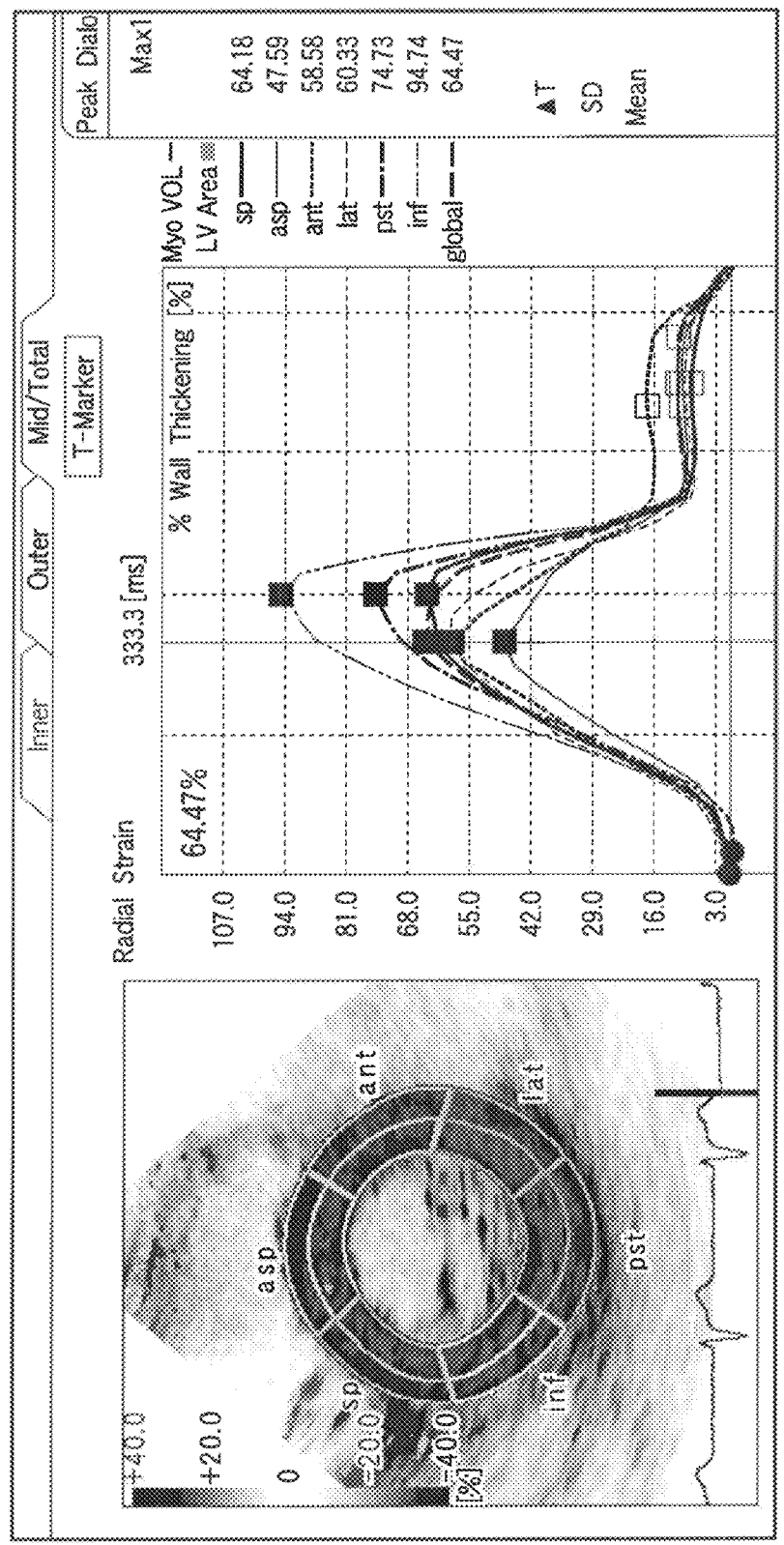
FIG. 9 is a diagram illustrating the effect obtained by the ultrasonic diagnostic apparatus according to the first embodiment.
Figure 10:
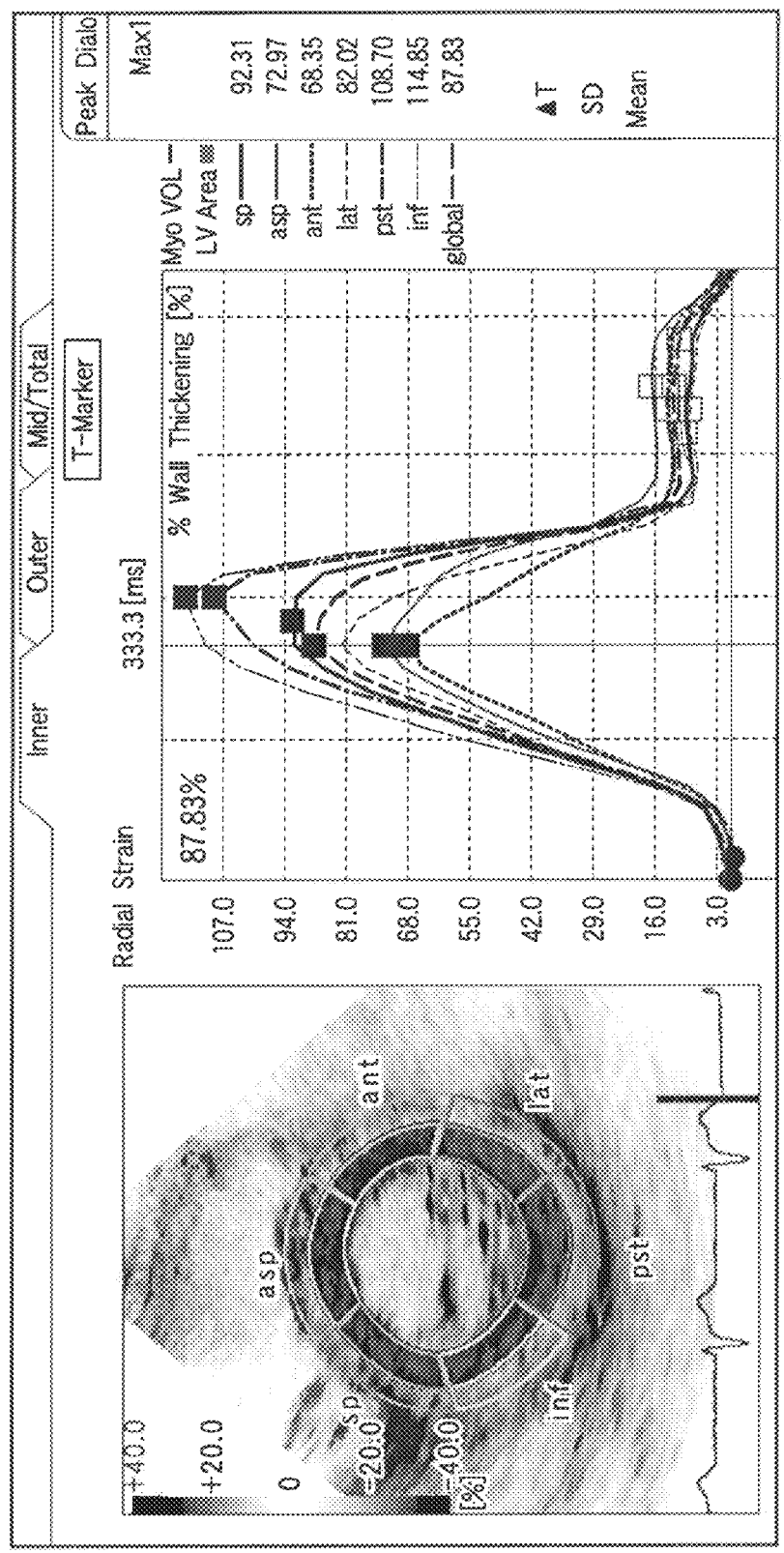
FIG. 10 is a diagram illustrating the effect obtained by the ultrasonic diagnostic apparatus according to the first embodiment.
Figure 11:
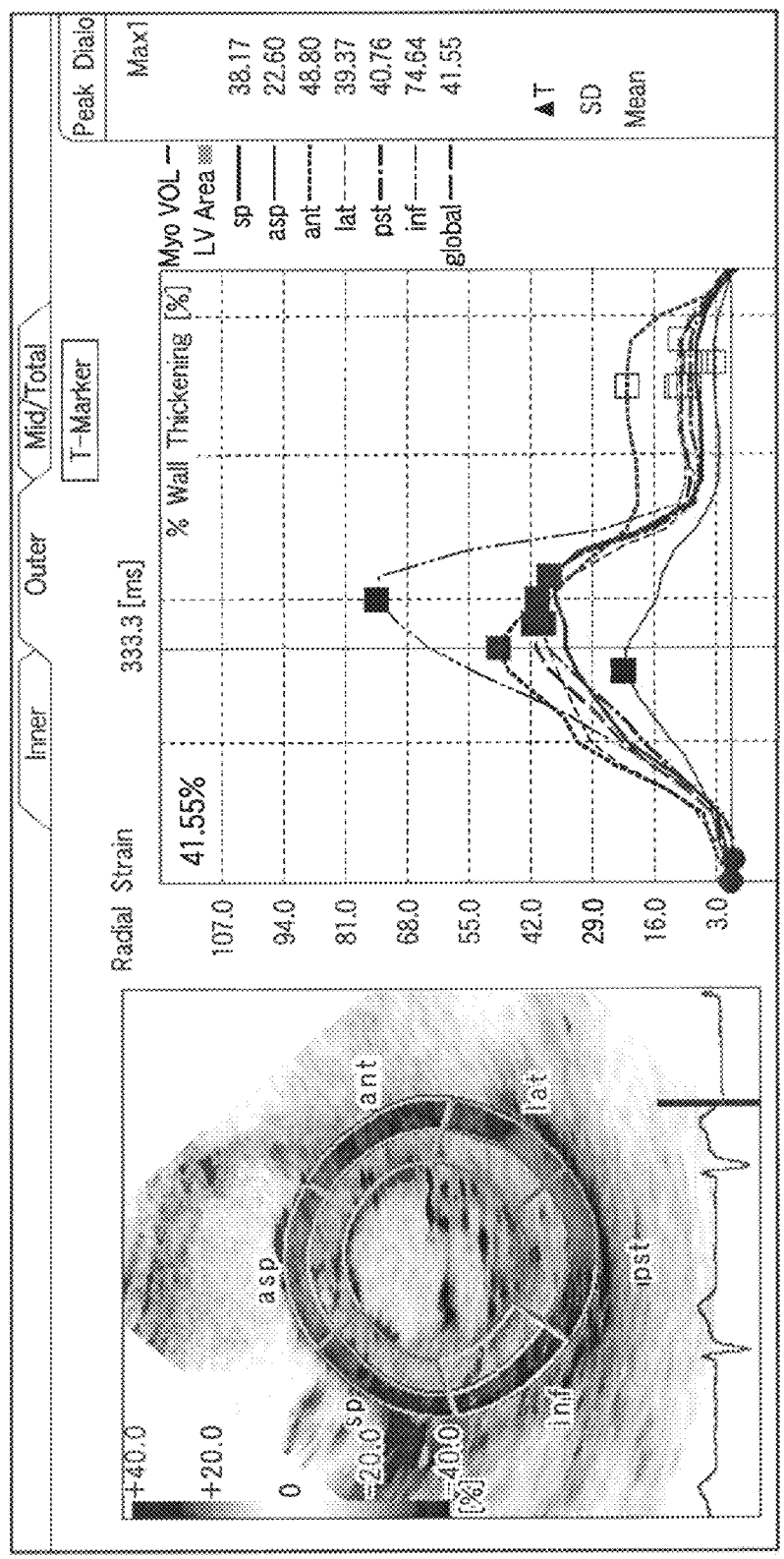
FIG. 11 is a diagram illustrating the effect obtained by the ultrasonic diagnostic apparatus according to the first embodiment.

FIGS. 6 to 11 are diagrams more specifically illustrating the second effect. FIGS. 6 to 8 show an analysis example of the RS (t) information in a normal example obtained by the method of the related art. FIGS. 9 to 11 show an analysis example of the RS (t) information of the same data obtained by the ultrasonic diagnostic apparatus according to the invention. The image is displayed so as to be superimposed with the B-mode image by converting the RS (ES) value at the time phase ES into a color code. The graph shows the change of the RS (t) corresponding to each region of six segments divided in the circumferential direction and the change of the global RS (t) as the average in the entire regions. In addition, FIGS. 6 and 9 show results corresponding to the RS_total (t) between the endocardium and the epicardium, FIGS. 7 and 10 show results corresponding to the RS_inner (t) of only the side of the endocardium (between the endocardium and the middle layer), and FIGS. 8 and 11 show results corresponding to the RS_outer (t) of only the side of the epicardium (between the middle layer and the epicardium). In addition, the % value in the drawings indicates the global peak value of the RS (t).

As shown in FIGS. 6 to 11, in the case where the inner/outer ratio of the RS is obtained by using the global peak value of the RS (t), the inner/outer ratio is 1.2 in the related art, but is 2.1 in the ultrasonic diagnostic apparatus according to the invention. It is thought that the inner/outer ratio according to the ultrasonic diagnostic apparatus of the invention is closer to that in the existing clinical knowledge (the endocardium expands and contracts about two times a variation in the epicardium in the case of a healthy patient).

In addition, in the example shown in FIGS. 6 to 11, the division regions of the segment and the positions of the endocardium, the epicardium, and the middle layer are displayed as the frame line on the image. In the related art shown in FIGS. 6 to 8, since the segments are divided at the ES as described above using the strain gauge, each region is equally divided so as to be perpendicular to the wall. On the contrary, in the ultrasonic diagnostic apparatus according to the invention, since the segments are divided at the ED, as shown in FIGS. 9 to 11, the division lines are not always perpendicular to the wall at the ES, and each region may not be equally divided. This is the effect in accordance with the reference time phase changed to the ED described in the first effect.

Particularly, when the position of the middle layer is carefully observed, in the related art shown in FIGS. 6 to 8, since the position of the middle layer is always located at the middle position between the endocardium and the epicardium at the ES, it is difficult to intuitively recognize which one of the endocardium and the epicardium is contributing more to the radial strain. However, in the ultrasonic diagnostic apparatus, as apparently shown in the posterior wall and the interior wall shown in FIGS. 9 to 11, it is possible to immediately recognize the state where the radial strain of the endocardium is larger than that of the epicardium at the ES.

Second Embodiment

Next, a second embodiment of the invention will be described. In the first embodiment, "the normal retracking process from the ED1 to the ES" of the tracking point of the middle layer and the contours of the endocardium and the epicardium rearranged at the ED1 is performed, and then the normal tracking process (ST process) is performed until the ED2. On the contrary, in the second embodiment, instead of the normal retracking process from the ED1 to the ES, the movement information of the inner and outer cardiac walls is accurately created and evaluated in such a manner that "the initial reverse tracking process of plural middle layer path candidates is performed from the ES to the ED1 and the path passing through the tracking points on the middle layer and the contours of the endocardium and the epicardium rearranged at the ED1 is searched".

Figure 13:
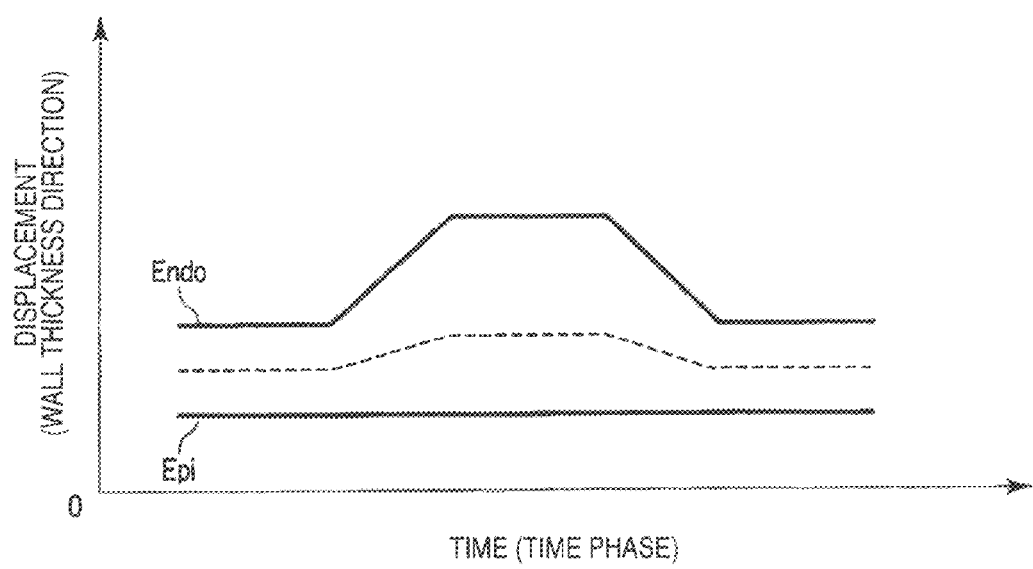
FIG. 13 is a diagram illustrating the tracking process including the reverse tracking process, the rearrangement process, and the retracking process according to the second embodiment.
Figure 14A:
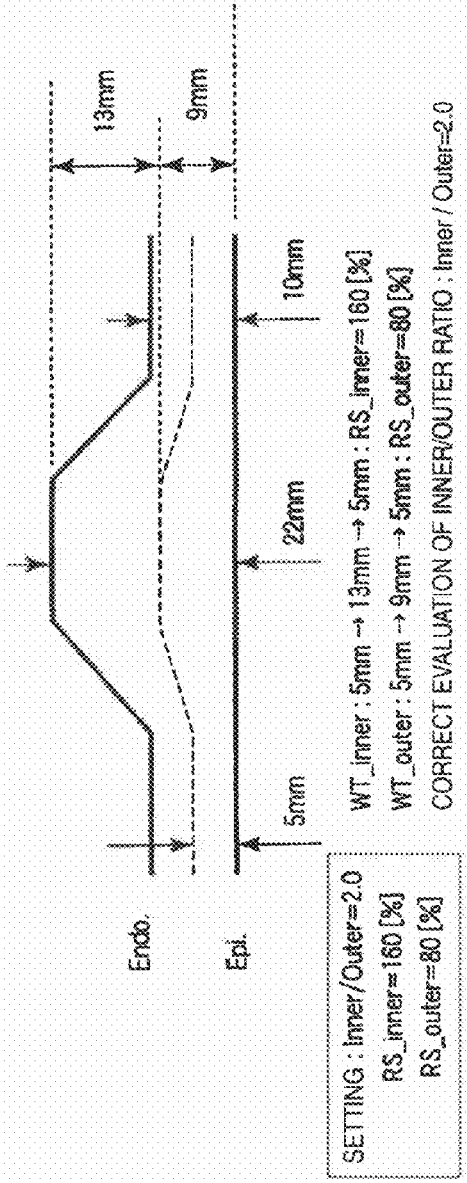
FIGS. 14A and 14B are diagrams illustrating a problem to be solved by the invention.
Figure 14B:
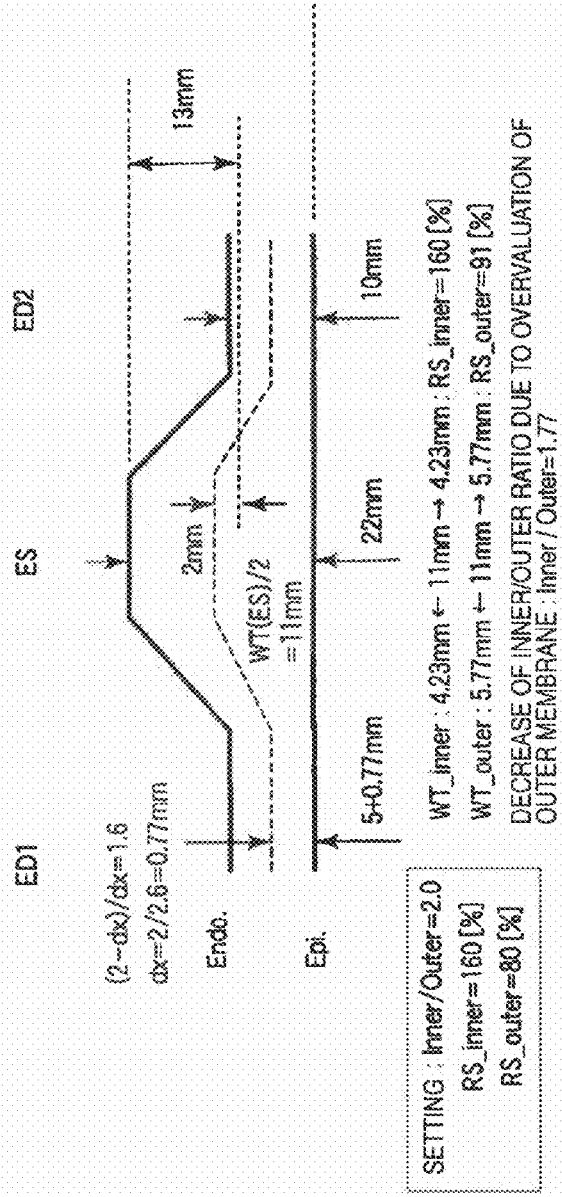

The second embodiment is different from the first embodiment in that the contents in Step S2 of FIG. 2 are different. Hereinafter, the contents in Step S2 will be mainly described. In addition, in the second embodiment, an example of a one-dimensional model shown in FIG. 13 will be described to help the understanding.

Figure 12:
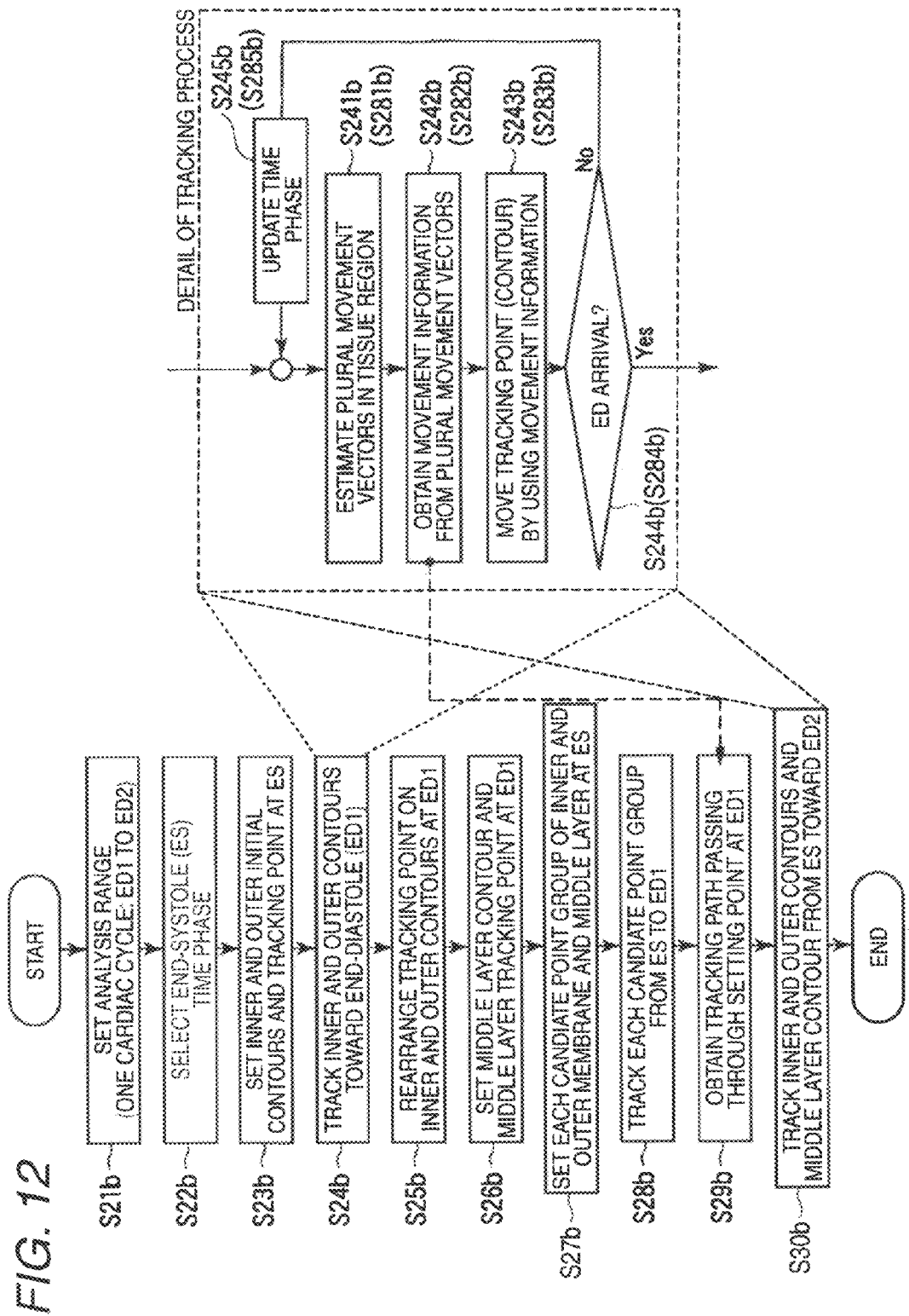
FIG. 12 is a flowchart showing a detailed sequence of a tracking process including a reverse tracking process, a rearrangement process, and a retracking process according to a second embodiment.

FIG. 12 is a flowchart showing a detailed sequence of the tracking process including the reverse tracking process, the rearrangement process, and the retracking process according to the second embodiment. In order to perform the process shown in FIG. 12, the control unit 31 shown in FIG. 1 sets a movement information analysis range of one heartbeat (ED1 to ED2) in the time-series two-dimensional image data, and selects the time phase ES (End-Systole time phase) in the one heartbeat (Step S21b and Step S22b). In addition, as in the first embodiment, a method of setting the one heartbeat (ED1 to ED2) and selecting the time phase ES is not particularly limited.

Subsequently, when the tracking point as the target of the tracking process and the initial inner and outer contours are set at the time phase ES (Step S23b), the movement vector processing unit 19 performs the reverse tracking process of the inner and outer contours (that is, the tracking point) toward the time phase ED1 (End-Diastole), and obtains the coordinate information of the configuration points of the inner and outer contours at each time phase (Step S24b). The detailed contents of the tracking process are substantially the same as those of the first embodiment (Step S241b to Step S245b).

Subsequently, the movement vector processing unit 19 rearranges the tracking point Epi (ED1, i) on the contour of the epicardium in the normal direction about the position of the endocardium as a reference (Step S25b), and sets the position of the middle layer Mid (ED1, i) for the tracking point so that the position of the middle layer, connecting the rearranged tracking point Epi (ED1, i) and the corresponding tracking point Endo (ED1, i) on the contour of the endocardium, divides the wall thickness direction into two segments (Step S26b). Here, "i" is a suffix for distinguishing plural positions of the endocardium (and the corresponding positions of the epicardium). However, in the case of the one-dimensional model shown in FIG. 13, the Epi (ED1, i) after the rearrangement process is at the same position as before the rearrangement process since there is only one "i" of the tracking point. In addition, the position of the epicardium is rearranged about the position of the endocardium as a reference, but as in the first embodiment, the rearrangement method is not limited thereto.

Subsequently, the movement vector processing unit 19 sets the candidate point group of the middle layer surrounded at the position of the endocardium $-\alpha$ and the position of the epicardium $+\alpha$ among the line segments passing through the Endo (ES, i) at the time phase ES (Step S27b). Here, $\alpha$ is set to an appropriate value larger than zero and smaller than a half of the wall thickness. This is because the position of the middle layer passing through the Mid (ED1, i) always passes through the candidate point group among the line segments at ES in the case of one dimension. Subsequently, the movement vector processing unit 19 performs the retracking process of each candidate point from the time phase ES to the time phase ED1 by using the movement information already obtained in Step S24b (Step S28b). As a result, the movement vector processing unit 19 adopts the candidate point passing through a position the closest to the Mid (ED, i) at the time phase ED1 as the actual position of the middle layer Mid (ES, i) at the time phase ES from the candidate point group. Accordingly, the position of the middle layer at each time phase between the time phase ED1 and the time phase ES for the tracking point i can be set by using the path through which the candidate point passes through the reverse tracking process.

Here, it is necessary to pay attention to the point that there is a high possibility that plural candidate points may pass through Mid (ED, i) since the wall thickness at time phase ES is generally larger than that at the time phase ED. In this case, it is desirable that the position of the middle layer is set to an average position of plural candidates.

Subsequently, the movement vector processing unit 19 obtains the coordinate information of the configuration points of the inner and outer contours at all time phases for one heartbeat by performing the tracking process from the time phase ES toward the time phase ED2 using the Mid (ES, i) set at the time phase ES and the Epi (ES, i) corresponding to the epicardium after the rearrangement process at the Endo (ES, i) (Step S28b). In addition, the contents of the tracking process are substantially the same as those in Step S241a to Step S245a.

In addition, if the basic concept is expanded to two dimensions or three dimensions, even when the initial contour is set at the time phase ES, it is possible to obtain the tracking path passing through the position of the middle layer divided into two segments at the time phase ED. However, as shown in the first embodiment, it is not possible to guarantee that the actual Mid (ES, i) at the time phase ES and the Epi (ES, i) corresponding to the epicardium after the rearrangement process pass through the line segment passing through the Endo (ES, i). Accordingly, in the case of two dimensions, a region including a two-dimensional expansion including the Endo (ES, i) is set to the middle layer and the candidate point group where the tracking point of the epicardium after the rearrangement process passes, and the searching process of both the middle layer and the epicardium may be performed. In the same manner, in the case of three dimensions, a region including a certain three-dimensional expansion including the Endo (ES, i) is set to the middle layer and the candidate point group where the tracking point of the epicardium passes, and the searching process of both the middle layer and the epicardium may be performed.

Also in the above-described configuration, it is possible to realize the same effects as those of the first embodiment including the first effect (the time phase as the observation reference is changed from the ES to the ED) and the second effect (the position of the middle layer is tracked by dividing the inner and outer positions into two segments at the ED).

Third Embodiment

In the first and second embodiments, basically, the application example in the case of the two-dimensional image is described. However, the technical spirit of the invention may be applied to the case where the three-dimensional ST process is performed on the three-dimensional image. Here, the case where the three-dimensional ST process is performed on the three-dimensional image is disclosed in, for example, Japanese Unexamined Patent Application Publication No. 2003-250804. In addition, in this case, the display example of the strain gauge in which the endocardium and the epicardium are separated is disclosed in Japanese Patent Application No. 2008-160744 and the like. Accordingly, even in the case where the three-dimensional ST process is performed on the three-dimensional image so as to perform the separate analysis of the endocardium and the epicardium by expanding the concept shown in the first embodiment or the second embodiment to three dimensions, it is possible to realize the same effects shown in the first and second embodiments.

In addition, the invention is not limited to the above-described embodiments, but the constituents thereof may be modified within the scope not departing from the spirit of the invention. For example, detailed modified examples are shown as below.

(1) The functions according to the embodiments may be realized in such a manner that a program performing the process is installed in a computer such as a workstation and is loaded on a memory. At this time, a program capable of performing the method using the computer may be distributed while being stored in a storage medium such as a magnetic disk (a floppy (trademark) disk, a hard disk, and the like), an optical disk (a CD-ROM, a DVD, and the like), and a semiconductor memory.

(2) A series of the process procedure in the above-described embodiments may be performed in such a manner that video data of a heart for at least one heartbeat is obtained by the ultrasonic diagnostic apparatus, the cine data is transmitted to a computer such as a PC or a workstation, and the process may be performed separately from the ultrasonic diagnostic apparatus. Alternatively, cine data of a heart may be temporarily stored, the storage data may be read from the ultrasonic diagnostic apparatus or the computer, and then a series of the processes introduced in the embodiments may be performed.

In addition, in the above-described embodiments, a case is exemplified in which the process in accordance with the movement information creating function is performed by using the cine data of the heart for at least one heartbeat obtained by the ultrasonic diagnostic apparatus. However, the technical spirit of the invention is not limited to this example. For example, the process in accordance with the movement information creating function according to the above-described embodiments may be performed by using cine data of the heart for at least one heartbeat obtained using a medical image diagnostic apparatus represented by an X-ray computed tomography imaging apparatus and a magnetic resonance imaging apparatus other than the ultrasonic diagnostic apparatus. In addition, image data obtained by these medical image diagnostic apparatuses may be transmitted to a computer such as a PC or a workstation so as to perform the process while being separated from the medical image diagnostic apparatuses.

(3) In the above-described embodiments, an example is described in which the middle layer is set to one position, but the middle layer may be set to two or three positions in correspondence to the multi-layer structure of the myocardium so as to perform a more detailed wall movement analysis.

(4) Regarding a tissue as a target, the invention may be applied to an example other than the cardiac wall, such as a periodically moving portion, an internal organ, or a blood vessel wall. Particularly, in the application to an artery, when a strain degree for a plaque growing mainly in the endocardium or the intima-media complex (IMT) is observed in detail while being divided into plural segments, it is expected that the invention will contribute to detailed diagnosis of the arteriosclerosis.

Further, various inventions may be contrived by the appropriate combination of the plural constituents disclosed in the above-described embodiments. For example, several constituents may be omitted from all the constituents shown in the above-described embodiments. In addition, the constituents of the different embodiments may be appropriately combined.

What is claimed is:

1. An ultrasonic diagnostic apparatus, comprising:
a data obtaining circuit which scans a periodically moving patient diagnosis portion through an ultrasonic wave and obtains two-dimensional or three-dimensional spatial receiving signals for a first predetermined period equal to or more than one period; and
a processing circuit which creates two-dimensional or three-dimensional time-series ultrasonic image data by using the spatial receiving signals, sets regions of interest (ROIs) corresponding to inner and outer layers of a tissue of the patient diagnosis portion on the ultrasonic image data at a first time, performs a first tracking process to obtain position information of the ROIs at each time during a second predetermined period that starts from the first time and extends back toward a second time before the first time, based on movement information during the second predetermined period, sets positions of one or more middle layers in the ROIs of the ultrasonic image data at the second time before the first time, and performs a second tracking process to obtain position information of the middle layers at a predetermined time based on the movement information and the second time,
wherein the second tracking process is different from the first tracking process.

2. The ultrasonic diagnostic apparatus according to claim 1,
wherein the processing circuit sets the positions of the middle layers in such a manner that one point is set on the outer or inner layer so as to make a pair, corresponding to a local thickness between the inner and outer layer in a normal vector direction, with a certain point on the corresponding inner or outer layer, and a distance between the pair corresponding to the thickness is equally divided.

3. The ultrasonic diagnostic apparatus according to claim 1,
wherein the processing circuit performs the second tracking process from the second time as a start time.

4. The ultrasonic diagnostic apparatus according to claim 1,
wherein the processing circuit sets candidate points at plural positions of the middle layers in an inside of the ROIs set at the first time, selects a tracking path based on the positions of the middle layers expected at the second time among plural tracking paths corresponding to the candidate points at plural positions obtained by the first tracking process and performs the second tracking process by using the selected tracking path.

5. The ultrasonic diagnostic apparatus according to claim 1, wherein the processing circuit obtains the movement information by using a movement vector estimating process including a pattern matching process.

6. The ultrasonic diagnostic apparatus of claim 1, wherein the processing circuit is configured to perform the second tracking process so that a time direction of tracking in the first tracking process is opposite to a time direction of tracking in the second tracking process.

7. The ultrasonic diagnostic apparatus according to claim 1, wherein:
the processing circuit creates a movement information image in which movement information defined by using at least the position information of the middle layers is displayed while being superimposed or arranged with the ultrasonic image data in a predetermined form, and causes a display to display the created movement information image.

8. The ultrasonic diagnostic apparatus according to claim 7,
wherein the processing circuit sets a frame line formed by a position of a thickness-direction division line for dividing a contour position of at least one of the ROIs corresponding to the inner and outer layers, contour positions corresponding to the one or more middle layers, and the ROIs into a predetermined number of segments, and creates the movement information image in which the frame line is superimposed with a corresponding position on the ultrasonic image data at each time during the second predetermined period.

9. The ultrasonic diagnostic apparatus according to claim 7,
wherein the processing circuit sets a predetermined number of strain gauges formed by plural line segments connecting two end points in the ROIs corresponding to the inner and outer layers with one or more middle layer points existing between the end points obtained by the second tracking process, and creates a strain gauge image, in which each strain gauge is superimposed with a corresponding position on the ultrasonic image data at each time during the second predetermined period, as the movement information image.

10. An ultrasonic image processing apparatus, comprising:
a storage which stores two-dimensional or three-dimensional spatial receiving signals, obtained by scanning a periodically moving patient diagnosis portion through an ultrasonic wave, for a first predetermined period equal to or more than one period; and
a processing circuit which sets regions of interest (ROIs) corresponding to inner and outer layers of a tissue of the patient diagnosis portion on two-dimensional or three-dimensional time-series ultrasonic image data by using the spatial receiving signals, performs a first tracking process to obtain position information of the ROIs at each time during a second predetermined period that starts from a first time and extends back toward a second time before the first time, based on movement information, during the second predetermined period, sets positions of one or more middle layers in the ROIs of the ultrasonic image data at the second time before the first time, and performs a second tracking process to obtain position information of the middle layers at a predetermined time based on the movement information and the second time,
wherein the second tracking process is different from the first tracking process.

11. The ultrasonic image processing apparatus according to claim 10,
wherein the processing circuit sets the positions of the middle layers in such a manner that one point is set on the outer or inner layer so as to make a pair, corresponding to a local thickness between the inner and outer layers in a normal vector direction, with a certain point on the corresponding inner or outer layer, and a distance between the pair corresponding to the thickness is equally divided.

12. The ultrasonic image processing apparatus according to claim 10,
wherein the processing circuit performs the second tracking process from the second time as a start time.

13. The ultrasonic image processing apparatus according to claim 10,
wherein the processing circuit sets candidate points at plural positions of the middle layers in an inside of the ROIs set at the first time, selects a tracking path based on the positions of the middle layers expected at the second time among plural tracking paths corresponding to the candidate points at plural positions obtained by the first tracking process and performs the second tracking process by using the selected tracking path.

14. The ultrasonic image processing apparatus according to claim 10, wherein:
the processing circuit creates a movement information image in which movement information defined by using at least the position information of the middle layers is displayed while being superimposed or arranged with the ultrasonic image data in a predetermined form, and causes a display to display the created movement information image.

15. The ultrasonic image processing apparatus according to claim 14,
wherein the processing circuit sets a frame line formed by a position of a thickness-direction division line for dividing a contour position of at least one of the ROIs corresponding to the inner and outer layers, contour positions corresponding to the one or more middle layers, and the ROIs into a predetermined number of segments, and creates the movement information image in which the frame line is superimposed with a corresponding position on the ultrasonic image data at each time during the second predetermined period.

16. The ultrasonic image processing apparatus according to claim 14,
wherein the processing circuit sets a predetermined number of strain gauges formed by plural line segments connecting two end points in the ROIs corresponding to the inner and outer layers with one or more middle layer points existing between the end points obtained by the second tracking process, and creates a strain gauge image, in which each strain gauge is superimposed with a corresponding position on the ultrasonic image data at each time during the second predetermined period, as the movement information image.

17. A medical image diagnostic apparatus, comprising:
a data obtaining circuit which obtains two-dimensional or three-dimensional time-series image data of a periodically moving patient diagnosis portion for a first predetermined period equal to or more than one period;
a processing circuit which sets regions of interest (ROIs) corresponding to inner and outer layers of a tissue of the patient diagnosis portion on the image data at a first time during the first predetermined period, performs a first tracking process to obtain position information of the ROIs at each time during a second predetermined period that starts from the first time and extends back toward a second time before the first time, based on movement information, at each time and the first time, sets positions of one or more middle layers in the ROIs of the image data at the second time before the first time, and performs a second tracking process to obtain position information of the middle layers at each time during the second predetermined period based on the movement information and the second time,
wherein the second tracking process is different from the first tracking process.

18. A medical image processing apparatus, comprising:
a storage which stores two-dimensional or three-dimensional time-series image data of a periodically moving patient diagnosis portion for a first predetermined period equal to or more than one period;

a processing circuit which sets regions of interest (ROIs) corresponding to inner and outer layers of a tissue of the patient diagnosis portion on the image data at a first time during the first predetermined period, performs a first tracking process to obtain position information of the ROIs at each time during a second predetermined period that starts from the first time and extends back toward a second time before the first time, based on movement information, during the second predetermined period, sets positions of one or more middle layers in the ROIs of the image data at the second time before the first time, and performs a second tracking process to obtain position information of the middle layers at a predetermined time, wherein the second tracking process is different from the first tracking process.

19. An ultrasonic image processing method which is performed on two-dimensional or three-dimensional spatial receiving signals, obtained by scanning a periodically moving patient diagnosis portion, for a first predetermined period equal to or more than one period, the ultrasonic image processing method comprising:

setting regions of interest (ROIs) corresponding to inner and outer layers of a tissue of the patient diagnosis portion on two-dimensional or three-dimensional time-series ultrasonic image data by using the spatial receiving signals;

performing a first tracking process to obtain position information of the ROIs at each time during a second predetermined period that starts from the first time and extends back toward a second time before the first time, based on movement information during the second predetermined period;

setting positions of one or more middle layers in the ROIs of the ultrasonic image data at the second time before the first time; and performing a second tracking process to obtain position information of the middle layers at a predetermined time based on the movement information and the second time, wherein the second tracking process is different from the first tracking process.

20. The ultrasonic image processing method according to claim 17, wherein in the setting positions of one or more middle layers, the positions of the middle layers are set in such a manner that one point is set on the outer or inner layer so as to make a pair, corresponding to a local thickness between the inner and outer layers in a normal vector direction, with a certain point on the corresponding inner or outer layer, and a distance between the pair corresponding to the thickness is equally divided.

21. The ultrasonic image processing method according to claim 19, wherein in the second tracking process, the second tracking process at each time during the second predetermined period is performed from the second time as a start time.

22. The ultrasonic image processing method according to claim 19, wherein in the second tracking process, candidate points are set at plural positions of the middle layers in an inside of the ROIs set at the first time;

a tracking path is selected based on the positions of the middle layers expected at the second time among plural tracking paths corresponding to the candidate points at plural positions obtained by the first tracking process; and the second tracking process is performed by using the selected tracking path.

23. The ultrasonic image processing method according to claim 19, further comprising:

creating a movement information image in which movement information defined by using at least the position information of the middle layers is displayed while being superimposed or arranged with the ultrasonic image data in a predetermined form; and displaying the created movement information image.

24. The ultrasonic image processing method according to claim 23, further comprising:

setting a frame line formed by a position of a thickness-direction division line for dividing a contour position of at least one of the ROIs corresponding to the inner and outer layers, contour positions corresponding to the one or more middle layers, and the ROIs into a predetermined number of segments; and creating the movement information image in which the frame line is superimposed with a corresponding position on the ultrasonic image data at each time during the second predetermined period.

25. The ultrasonic image processing method according to claim 23, further comprising setting a predetermined number of strain gauges formed by plural line segments connecting two end points in the ROIs corresponding to the inner and outer layers with one or more middle layer points existing between the end points obtained by the second tracking process; and creating a strain gauge image, in which each strain gauge is superimposed with a corresponding position on the ultrasonic image data at each time during the second predetermined period, as the movement information image.

26. A medical image processing method which is performed on two-dimensional or three-dimensional time-series image data obtained from a periodically moving patient diagnosis portion for a first predetermined period equal to or more than one period, the medical image processing method comprising:

setting regions of interest (ROIs) corresponding to inner and outer layers of a tissue of the patient diagnosis portion on the image data at a first time during the first predetermined period;

performing a first tracking process to obtain position information of the ROIs at each time during a second predetermined period that starts from the first time and extends back toward a second time before the first time, based on movement information during the second predetermined period;

setting positions of one or more middle layers in the ROIs of the image data at the second time before the first time; and performing a second tracking process to obtain position information of the middle layers at a predetermined time based on the movement information and the second time, wherein the second tracking process is different from the first tracking process.

* * * * *